United States Patent [19]

Lee et al.

[11] Patent Number: 4,655,816
[45] Date of Patent: Apr. 7, 1987

[54] HERBICIDAL 2-TRIFLUOROMETHYL 3-PYRIDINE CARBOXYLIC ACID DERIVATIVES

[75] Inventors: Len F. Lee, St. Charles; Maria L. Miller, Manchester, both of Mo.

[73] Assignee: Monsanto Company, St. Louis, Mo.

[21] Appl. No.: 768,660

[22] Filed: Aug. 27, 1985

Related U.S. Application Data

[63] Continuation-in-part of Ser. No. 668,928, Nov. 6, 1984, abandoned.

[51] Int. Cl.$^4$ .................... A01N 57/16; A01N 43/40; C07D 213/80; C07D 401/12
[52] U.S. Cl. ............................ 71/86; 71/87; 71/94; 546/298; 546/25; 546/24; 546/281; 546/292
[58] Field of Search .................. 546/25, 24, 298, 281, 546/292; 71/94, 87, 86

[56] References Cited

U.S. PATENT DOCUMENTS

| | | | |
|---|---|---|---|
| 3,629,270 | 12/1971 | Gante | 546/283 |
| 3,651,070 | 3/1972 | Granito | 546/326 |
| 3,705,170 | 12/1972 | Torba | 71/94 |
| 4,249,009 | 2/1981 | Bailey | 546/298 |

Primary Examiner—Henry R. Jiles
Assistant Examiner—Dale A. Bjorkman
Attorney, Agent, or Firm—James C. Bolding

[57] ABSTRACT

There are disclosed novel 2,6-substituted-3-pyridinecarboxylic acids, esters, and salts useful as herbicides, and as intermediates which provide herbicides.

36 Claims, No Drawings

HERBICIDAL 2-TRIFLUOROMETHYL 3-PYRIDINE CARBOXYLIC ACID DERIVATIVES

This is a continuation-in-part of application Ser. No. 668,928, filed Nov. 6, 1984, abandoned.

This invention relates to a new class of 2,6-substituted pyridinecarboxylic acid derivatives having a wide range of activity as herbicides as well as utility as herbicide intermediates.

Pyridine derivatives have, for many years, been investigated for use in the biological sciences. For example, 2,6-bis-(trifluoromethyl)-4-pyridinols have been found useful as herbicides and fungicides as disclosed in U.S. Pat. No. 3,748,334. Such compounds are characterized by substitution in the 4-position by a hydroxyl radical. In addition to the hydroxyl radical, the pyridine nucleus may also be substituted with bromo, chloro or iodo radicals. Trifluoromethyl pyridine derivatives have also been disclosed in U.S. Pat. Nos. 2,516,402 and 3,705,170 wherein the nucleus is further substituted by halogens as well as numerous other substituents. Some of these compounds are also noted to be useful as herbicides.

Also known because of their fungicidal activity are 4-substituted 2,6-dichloro-3,5-dicyanopyridines wherein the 4-position is substituted with alkyl, phenyl, naphthyl or pyridyl groups. Such compounds are disclosed in U.S. Pat. No. 3,284,293, while similar compounds are disclosed in U.S. Pat. No. 3,629,270 wherein the 4-position is substituted with a heterocyclic group wherein the hetero atom is oxygen or sulfur.

In EPO Pat. No. 44,262 there are disclosed 2,6-dialkyl-3-phenylcarbamyl-5-pyridinecarboxylates and -5-cyano-compounds useful as herbicides. There is no disclosure of the 2-haloalkyl radicals nor any substitution in the 4-position of the pyridine ring.

The pyridine derivatives have also received attention in the search for new herbicides and have been reported in U.S. Pat. Nos. 1,944,412, 3,637,716, and 3,651,070. All of these patents disclose polyhalo derivatives of dicarboxypyridines. All have in common the direct substitution on a ring carbon by a halogen in the 3- and 5-positions while the 2- and 6-positions are occupied by carboxylate groups. The 4-position is open to substitution by a wide range of materials including halogens, hydroxy radicals, alkoxy, and carboxyl groups. Such compounds have found utilization as herbicides, bactericides, and fungicides. When the 4 position is occupied by a silver salt, U.S. Pat. No. 1,944,412 discloses that such compounds have been utilized in the production of X-ray pictures with intravenous injection of such compounds.

BRIEF DESCRIPTION OF THE INVENTION

It is an object of this invention to provide herbicidal methods and compositions utilizing the novel pyridines of this invention.

Another object of this invention is to provide novel methods for preparing the novel compounds of this invention and novel intermediates useful therein.

The novel compounds of this invention are useful as herbicides or intermediates which can be converted to herbicides and represented by the generic formula

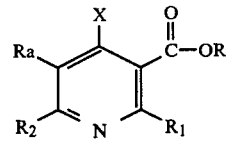

wherein:

R is selected from the group consisting of hydrogen, lower alkyl, lower alkenyl, lower alkynyl, haloalkyl, haloalkenyl, and a cation;

$R_1$ is trifluoromethyl;

$R_2$ is selected from fluorinated methyl, chlorofluorinated methyl, and fluorinated ethyl radicals;

Ra is selected from hydrogen and lower alkyl radicals; and

X is selected from (a) a halogen selected from F, Cl, and Br;

(b) —$OR_3$ in which $R_3$ is selected from hydrogen, lower alkyl, lower alkenyl, lower alkynyl, $C_3$–$C_6$ cycloalkyl, $C_3$–$C_6$ cycloalkylalkyl, haloalkyl, aryl, aralkyl, dialkoxyphosphinyl, arylsulfonyl, lower alkylcarbonyl, lower $C_3$–$C_6$ cycloalkylcarbonyl, 3- to 6-membered ring saturated nitrogen containing heterocyclic carbonyl, lower haloalkylcarbonyl, arylcarbonyl, aralkylcarbonyl, aryloxyacetyl, arylcarbonylmethyl, carboalkoxymethyl, lower (dialkylamino)thioxo, lower dialkylaminocarbonyl, N-aryl-N-alkylaminocarbonyl, lower alkoxyphosphinothioyl, and a cation, (c) —$S(O)_nR_4$ in which n is an integer from 0–2 inclusive and $R_4$ is selected from lower alkyl, lower alkenyl, lower alkynyl, $C_3$–$C_6$ cycloalkyl, $C_3$–$C_6$ cycloalkylalkyl, haloalkyl, aryl, aralkyl and 3 to 6 membered ring saturated and unsaturated heterocycles and heterocycloalkyls, (d)

in which $R_5$ is selected from hydrogen, lower alkyl, lower haloalkyl, lower alkenyl, lower alkynyl, and haloalkenyl; and $R_6$ is selected from hydrogen, lower alkyl, lower haloalkyl, lower alkenyl, haloalkenyl, lower alkynyl, aryl, aralkyl, cyanoalkyl, dialkylamino, alkoxycarbonylalkyl, alkoxy, $C_3$–$C_6$ cycloalkyl, $C_3$–$C_6$ cycloalkylalkyl, haloalkylcarbonyl, 3–6 membered ring saturated and unsaturated heterocyclic alkyl, 3–6 membered ring saturated heterocycles, (e)

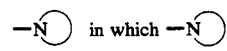

is a nitrogen containing saturated or unsaturated 3 to 8 membered heterocyclic ring moiety optionally containing one or more additional atoms selected from O, S, and N, and optionally substituted with one or more groups selected from lower alkyl and epoxy; and (f) azido.

The term "lower alkyl" means herein both straight and branched chain radicals having 1 to 7 carbon atoms which include, but are not limited to, ethyl, methyl, n-propyl, 1-ethylpropyl, 1-methylpropyl, n-butyl, 2,2-dimethylpropyl, pentyl, isobutyl, isopropyl. The term "cycloalkyl" is intended to mean saturated cyclic radicals such as cyclopropyl, cyclobutyl, cyclopentyl, and cyclohexyl.

The terms "lower alkenyl" and "lower alkynyl" herein mean alkenyl and alkynyl groups having 3 to 7 carbon atoms wherein the unsaturation is remote from the moiety attaching the lower alkenyl or alkynyl group to the pyridine ring. Examples of such alkenyl groups include 2-propenyl, 2-butenyl, 3-butenyl, 2-methyl-2-propenyl, and the like. Examples of such lower alkynyl groups include 2-propynyl, and so forth.

The term "haloalkyl" is intended to mean alkyl radicals substituted with one or more halogen atoms.

The term "cation" means any cation derived from a base providing a salt. Typical cations include, but are not limited to, alkali metals such as sodium, potassium, and lithium, alkaline earth metals such as calcium, organic amines, and anions such as ammonium, sulfonium, phosphonium and other salt complexes.

As used herein, "aryl" means a substituted or unsubstituted phenyl radical. Substituents include one or more halogen atoms, nitro radicals, lower alkyl, lower alkoxy, lower haloalkyl, lower haloalkoxy, and carbalkoxyalkoxy groups.

The term "nitrogen containing saturated or unsaturated 3 to 8 membered heterocyclic ring moiety optionally containing one or more additional atoms selected from O, S, and N, and optionally substituted with one or more groups selected from lower alkyl and epoxy" is intended to include radicals such as aziridinyl, piperidinyl, azetidinyl, pyrrolidinyl, hexahydroazepinyl, imidazolyl, pyrrolyl, triazolyl, pyrazolyl, optionally substituted with lower alkyl substituents as well as radicals such as

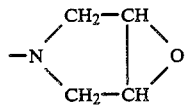

The term "fluorinated methyl" means herein methyl radicals having one or more fluorine atoms attached thereto including radicals wherein all hydrogen atoms are replaced by fluorine.

The term "chlorofluorinated methyl" means herein a methyl radical having at least one hydrogen replaced by fluorine and at least one other hydrogen replaced by chlorine.

DETAILED DESCRIPTION OF THE INVENTION

The route below schematically depicts a method whereby the pyridinemonocarboxylate compounds of this invention may be prepared from compounds which are readily available commercially. In this route, a 3-ketoester of the formula shown in which Ra is hydrogen or lower alkyl is reacted with trifluoroacetonitrile in the presence of a base. Examples of suitable bases are potassium t-butoxide, sodium in dimethoxyethane, sodium acetate, and the like. The result of this reaction is a 2-alkanoyl-3-amino-2-alkenoate ester; i.e., an enamine compound.

The enamine compound so produced is then reacted with 2-2.5 equivalents of a strong base, suitably lithium diisopropylamide to generate in situ a dianion which is then reacted with an ester of a carboxylic acid of the formula shown wherein $R_2$ is selected from perfluorinated methyl, perchlorofluorinated methyl, and perfluorinated ethyl groups. The reaction product is a mixture of a substituted 4-hydroxy-2-(trifluoromethyl)-6-[perfluorinated or perchlorofluorinated-(lower alkyl)]-3-pyridinecarboxylate and a substituted 2,3-dihydro-2-hydroxy-4-pyridone, which dehydrates readily when heated to form a 4-hydroxy-2-(trifluoromethyl)-6-[perfluorinated or perchlorofluorinated-(lower alkyl)]-3-pyridinecarboxylate of the present invention (Formula A).

The 4-hydroxy pyridine compounds shown in Formula A may be converted to a 4-alkoxy compound of this invention (Formula B) by alkylation with an alkyl halide in the presence of a base. Alkali metal carbonates or hydroxides, amines, and the like, are examples of suitable bases which promote the alkylation reaction.

The 4-halo-substituted compounds of this invention (Formula C) are prepared by reaction of the 4-hydroxypyridine with a chlorinating or brominating agent such as phosphorus oxychloride and phosphorus oxybromide in the presence of a suitable base. The 4-chloropyridines are intermediates in the preparation of compounds of this invention having a sulfur, nitrogen, or oxygen atom substituted at the 4-position on the pyridine ring.

Compounds according to the invention with sulfur substitution at the 4-position (Formula D) may be prepared by reaction of the 4-chloro compounds with a mercaptan in the presence of a base. The compounds of Formula D may then be oxidized, if desired, to compounds having $-SO_nR_4$ substitution at the 4-position. Suitable oxidizing agents include m-chloro-perbenzoic acid.

Nitrogen-substituted compounds are conveniently prepared from the 4-chloro pyridines by reaction with a primary or secondary amine, an alkali metal azide, or the like.

An alternative means of preparation of oxygen-substituted compounds of Formula B involves the 4-chloro-substituted compounds as an intermediate. In this alternate procedure the 4-chloropyridine is reacted with a compound having the formula $R_3OH$ in the presence of a base.

Compounds according to the invention with $R_2$ selected from difluoromethyl and fluoromethyl and provided that X is not chlorine may be prepared by hydrogenation of the compounds of this invention with $R_2$ selected from the corresponding chlorofluorinated methyl group.

A better appreciation of the present invention will be gained by reference to the following Examples.

As used throughout the specification, including the Examples, the following abbreviations have the following meanings:
LDA—lithium diisopropylamide
THF—tetrahydrofuran
DME—dimethoxyethane
DMF—N,N-dimethylformamide
MCPBA—m-chloroperbenzoic acid
HPLC—high pressure liquid chromatography
TLC—thin layer chromatography
n-BuLi—n-Butyl lithium
DMSO—dimethyl sulfoxide Pd/C—hydrogenation catalyst which is palladium deposited on finely - divided carbon.

Preparation of 4-Hydroxypyridinemonocarboxylate

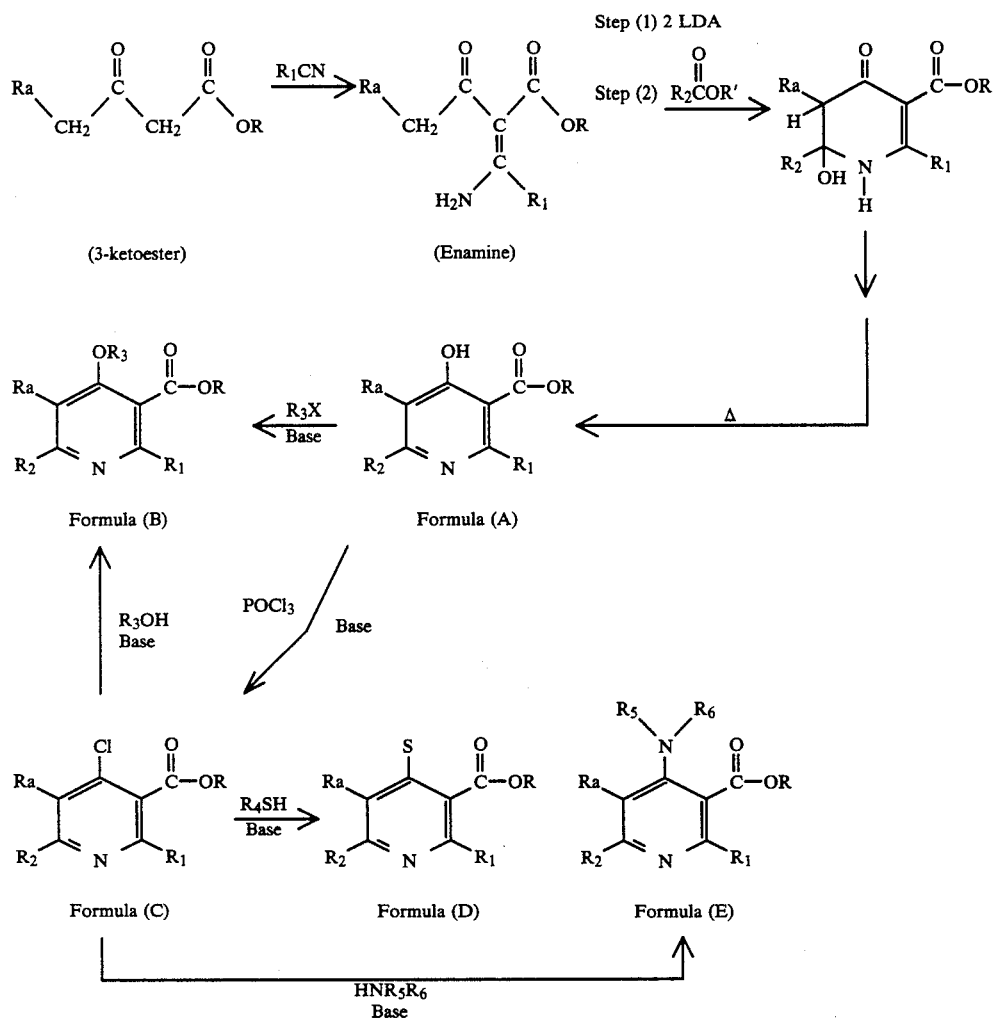

PREPARATION OF ENAMINE PRECURSOR COMPOUNDS

Example 1

Ethyl 2-acetyl-3-amino-4,4,4-trifluoro-2-butenoate

To a 1 liter, four-necked flask equipped with nitrogen inlet, thermometer, and mechanical stirrer was charged 499.74 g (490 ml, 3.84 mol) of ethyl acetoacetate and 12.9 g (0.115 mol) of potassium t-butoxide. The resulting mixture was stirred while 391 g (4.04 mol) of trifluoroacetonitrile was added. The reaction mixture was washed with hexane and the resulting solid was dried in vacuo affording 535 g (62%) of the enamine as a yellow solid; mp 63°-65° C.

Example 2

Methyl 2-acetyl-3-amino-4,4,4-trifluoro-2-butenoate

This compound was prepared as described in Example 1 (mp 70.5°-73.0°C.), except that methyl acetoacetate was employed as the starting beta-ketoester. All other reagents and conditions remained the same.

Anal. Calc'd. for $C_7H_8F_3N_1O_3$: C, 39.82; H, 3.82; N, 6.64; Found: C, 39.88; H, 3.83, N, 6.60

Compounds from Enamines

The following Examples 3-6 illustrate the preparation of compounds of Formula A in Route 1 by the reaction of an enamine compound from Example 1 or 2 with an appropriate fluorinated ester.

Example 3

Ethyl 2,6-bis(trifluoromethyl)-4-hydroxy-3-pyridinecarboxylate

To a flame dried 3-liter, four-necked flask equipped with nitrogen inlet, low temperature thermometer, 500 ml addition funnel and mechanical stirrer was charged 91.0 g (126 ml, 0.899 mol) of diisopropylamine and 500 ml of dry tetrahydrofuran. The resulting solution was cooled to −78° C. using an acetone-dry ice bath. To this was slowly added 383 ml (0.0880 mol) of 2.3M n-BuLi in hexane at such a rate that the reaction temperature was kept below −60° C. After stirring at −78° C. for 1 hour, a solution of 90.0 g (0.400 mol) of ethyl 2-acetyl-3-amino-4,4,4-trifluoro-2-butenoate from Example 1 in 150 ml of dry tetrahydrofuran was added in such a rate that the reaction temperature was kept below −60° C. The reaction mixture turned yellow and a solid suspension formed. After 1 hour of stirring at −78° C., the reation mixture was treated with 184.7 g (155 ml, 1.300 mol) of ethyl trifluoroacetate in such rate that the reaction temperature was kept below −60° C. This reaction mixture was left at −78° C. for 1 hour, then warmed to room temperature (the yellow suspension disappeared and a brown solution was formed) and stirred for 18 hours. The resulting solution was poured into 1.5 L of 10% HCl (aq.) and extracted 3 times with methylene chloride. The combined methylene chloride layers were dried (MgSO$_4$) and reduced in vacuo affording a thick brown oil. The residue was kugelrohr distilled at 47 Pa. The earlier fraction (pot temperature 50° C.) was discarded. The later fraction (pot temperature 80° C.) afforded 80.0 g (66%) of the pyridine product; mp 70°–77° C.

Anal. Calc'd. for $C_{10}H_7F_6N_1O_3$: C, 39.62; H, 2.33; N, 4.62; Found: C, 39.62; H, 2.37; N, 4.62

Example 4

Methyl 2,6-bis(trifluoromethyl)-4-hydroxy-3-pyridinecarboxylate

To a flame dried 3-liter, four-necked flask equipped with nitrogen inlet, low temperature thermometer, 500 ml addition funnel and mechanical stirrer is charged 147 ml (1.05 ml) of diisopropylamine and 600 ml of dry tetrahydrofuran. The resulting solution is cooled to −78° C. using an acetone-dry ice bath. To this is slowly added 618 ml (1.05 mol) of 1.7M n-BuLi in hexane at such a rate that the reaction temperature was kept below −60° C. After stirring at −78° C. for 1 hour, a solution of 106 g (0.50 mol) of methyl 2-acetyl-3-amino-4,4,4-tri-fluoro-2-butenoate from Example 2 in 400 ml of dry THF was added in such a rate that the reaction temperature was kept below −60° C. The reaction mixture turned yellow and a solid suspension formed. After 1 hour of stirring at −78° C., the reaction mixture was treated with 59.5 ml (0.50 mol) of ethyl trifluoroacetate in such rate that the reaction temperature was kept below −60° C. This reaction mixture was left at −78° C. for 1 hour, then warmed to room temperature (the yellow suspension disappeared and a yellow solution was formed) and stirred for 2 hours. The resulting solution was poured into 1 L of H$_2$O and extracted with ether (3×700 ml). The combined ether layers were washed with H$_2$O (2×800 ml) and the combined aqueous layers were acidified with concentrated HCl (pH~2). The acidified aqueous layer was extracted with CHCl$_3$ (3×1000 ml), dried (MgSO$_4$) and reduced in vacuo affording 120.85 g of a yellow solid. The crude was recrystallized from ether/hexane to give 103.28 g (71%) of pyridine product; mp 62°–75° C.

Anal. Calc'd. for $C_9H_5F_6N_1O_3$: C, 37.38; H, 1.74; N, 4.85; Found: C, 37.35; H, 1.74; N, 4.81

Example 5

Ethyl 6-(chlorodifluoromethyl)-4-hydroxy-2-(trifluoromethyl)-3-pyridinecarboxylate This pyridine compound was prepared as described in Example 3, but instead of using ethyl trifluoroacetate, 188 g (1.300 mol) of ethyl chlorodifluoroacetate were reacted affording 75 g (78%) of product after kugelrohr distillation at 60 Pa and pot temperature of 85° C.; mp 56.5°–58.5° C.

Anal. Calc'd. for $C_{10}H_7Cl_1F_5N_1O_3$: C, 37.58; H, 2.21; N, 4.38; Found: C, 37.30; H, 2.19; N, 4.19

Example 6

4-Hydroxy-2,6-bis(trifluoromethyl)-3-pyridinecarboxylic acid

A solution of ethyl 2,6-bis(trifluoromethyl)-4-hydroxy-3-pyridinecarboxylate (product of Example 3, 15 g, 0.0495 mol) in 5% aqueous sodium hydroxide (60 ml, 0.148 mol) was refluxed for 3 hours. The reaction was complete as judged by TLC (10% methanol in ethyl acetate). The mixture was then poured into a mixture of ice in concentrated aqueous hydrochloric acid and extracted with ethyl acetate. The ethyl acetate solution was dried over magnesium sulfate, and concentrated to give a light brown solid (13 g). It was treated with petroleum ether to give 11.9 g of a white solid (83%); mp 168°–172° C.

Anal. Calc'd. for $C_8H_3F_6N_1O_3$: C, 33.19; H, 1.60; N, 4.84; Found: C, 33.29; H, 1.44; N, 4.83

Preparation of 4-Alkoxypyridine Compounds from 4-Hydroxy Compounds

Pyridine monocarboxylate compounds of Formula B shown in Route 1 may be prepared from the 4-hydroxypyridine compounds of Examples 3–5 above via alkylation using a haloalkyl compound R$_3$X and a basic compound such as K$_2$CO$_3$ as is illustrated in the following Examples 7–18.

Example 7

Ethyl 2,6-bis(trifluoromethyl)-4-allyloxy-3-pyridinecarboxylate

A mixture of 6.06 g (0.02 mol) of product of Example 3, 2.8 g (0.02 mol) of K$_2$CO$_3$, 30 g of allyl bromide, and 50 ml of acetone was held at reflux for 4 hours and concentrated. The residue was treated with water and extracted into ether. The ether solution was dried and concentrated. The residue was kugelrohr distilled at 133 Pa (pot temperature 110° C.) to give 6.2 g (90%) of product, n$_D^{25}$ 1.4330.

Anal. Calc'd. for $C_{13}H_{11}F_6N_1O_3$: C, 45.49; H, 3.23; N, 4.08; Found: C, 45.48; H, 3.25; N, 4.06

Example 8

Ethyl 2,6-bis(trifluoromethyl)-4-methoxy-3-pyridinecarboxylate

A mixture of 8.0 g (0.0264 mol) of product of Example 3, 3.6 g (0.026 mol) of potassium carbonate, 20 g of methyl iodide, and 50 ml of acetone was held at reflux for 6 hours and concentrated. The residue was treated with water and extracted with ether. The ether extract was washed once with 30 ml of 10% NaOH, dried, and concentrated. The residue was crystallized from hexane to give 6.91 g (82.5%) of product; mp 58.5°–59.5° C.

Anal. Calc'd. for $C_{11}H_9F_6N_1O_3$: C, 41.65; H, 2.86; N, 4.42; Found: C, 41.33; H, 2.94; N, 4.36

Example 9

Ethyl 2,6-bis(trifluoromethyl)-4-benzyloxy-3-pyridinecarboxylate

A mixture of 6.06 g (0.02 mol) of product of Example 3, 16 g of benzyl bromide, 3 g of potassium carbonate and 50 ml of acetone was held at reflux for 2 hours and concentrated. The residue was treated with water and extracted with ether. The ether solution was dried and concentrated. The residue was kugelrohr distilled at 13 Pa (pot temperature 50° C.) to remove excess benzyl bromide. The residue was crystallized from hexane to give 6.4 g (81%) of product; mp 56°–58.5° C.

Anal. Calc'd for $C_{17}H_{13}F_6N_1O_3$: C, 51.91; H, 3.33; N, 3.56; Found: C, 51.96; H, 3.34; N, 3.54

Example 10

Ethyl 2,6-bis(trifluoromethyl)-4-isopropoxy-3-pyridinecarboxylate

Following the procedure of Example 8, this material was prepared in 74% yield from product of Example 3 and 2-iodopropane as a liquid, $n_D^{25}$ 1.4210.

Anal. Calc'd. for $C_{13}H_{13}F_6N_1O_3$: C, 45.23; H, 3.80; Found: C, 45.18; H, 3.79

Example 11

Ethyl 2,6-bis(trifluoromethyl)-4-ethoxy-3-pyridinecarboxylate

This material was prepared following the procedure of Example 8 in 77% yield from product of Example 3 and ethyl iodide as a white solid; mp 57°–59° C.

Anal. Calc'd. for $C_{12}H_{11}F_6N_1O_3$: C, 43.52; H, 3.35; Found: C, 43.56; H, 3.35

Example 12

Ethyl 6-(chlorodifluoromethyl)-4-methoxy-2-(trifluoromethyl)-3-pyridinecarboxylate This compound was prepared using the procedure of Example 8, 12.0 g (0.038 mol) of product of Example 5, 5.8 g (0.042 mol) of $K_2CO_3$, 12 ml (0.190 mol) of methyl iodide in 200 ml of acetone were reacted affording 11.21 g of solid which was purified by HPLC using 25% ethyl acetate/cyclohexane as eluting solvent to give 9.33 g (73.6%) of product as a white solid; mp 62°–64° C.

Anal. Calc'd. for $C_{11}H_9Cl_1F_5N_1O_3$: C, 39.60; H, 2.72; N, 4.20; Found: C, 39.69; H, 2.73; N, 4.15

Example 13

Ethyl 6-(chlorodifluoromethyl)-4-ethoxy-2-(trifluoromethyl)-3-pyridinecarboxylate This product was prepared as described in Example 8, 25. g (0.080 mol) of product of Example 5, 14.3 g (0.103 mol) of $K_2CO_3$, 37.5 ml (0.470 mol) of ethyl iodide in 100 ml of acetone were reacted affording 22.86 g of oil which was purified by HPLC using 3% ethyl acetate/cyclohexane as eluting solvent to give 14.73 g of solid. Crystallization in hot hexane gave 11.11 g (41.6%) of solid. A portion (0.98 g) of this solid was kugelrohr distilled at 29 Pa, pot temperature 70° C., to give 0.81 g of product as a white solid; mp 54.5°–56.5° C.

Anal. Calc'd. for $C_{12}H_{11}F_5Cl_1N_1O_3$: C, 41.46; H, 3.20; N, 4.03; Found: C, 41.57; H, 3.23; N, 4.02

Example 14

Ethyl 6-(chlorodifluoromethyl)-4-isopropoxy-2-(trifluoromethyl)-3-pyridinecarboxylate A mixture of 15.0 g (0.047 mol) of product of Example 5, 6.5 g (0.047 mol) of $K_2CO_3$ and 5.2 ml (0.52 mol) of 2-iodopropane in 100 ml of acetone was stirred at reflux for 64 hours. The cooled reaction mixture was concentrated in vacuo. The residue was dissolved in ether, washed with $H_2O$, dried ($MgSO_4$), and concentrated in vacuo to a brown oil which was kugelrohr distilled at 68 Pa, pot temperature 90° C., affording 15.11 g (88.9%) of product as a clear oil, $n_D^{25}$ 1.4405.

Anal. Calc'd. for $C_{13}H_{13}Cl_1F_5N_1O_3$: C, 43.20; H, 3.62; N, 3.87; Found: C, 43.03; H, 3.66; N, 3.86

Example 15

Ethyl 6-(chlorodifluoromethyl)-4-methoxycarbonylmethoxy)-2-(trifluoromethyl)-3-pyridinecarboxylate 0.8 hydrate A mixture of 25 g (0.078 mol) of product of Example 5, 13 g (0.094 mol) of $K_2CO_3$ and 7.4 ml (0.078 mol) of methyl bromoacetate in 125 ml of acetonitrile were refluxed for 64 hours. The cooled reaction mixture was concentrated in vacuo. The residue was poured into water, extracted with ether, washed with water, dried ($MgSO_4$) and concentrated in vacuo. The residue was recrystallized in hot hexane to give 23.49 g (76.9%) of solid. A portion of this solid (3.0 g) was recrystallized a second time in hot hexane affording 2.74 g of product as a beige solid; mp 67°–69° C.

Anal. Calc'd. for $C_{13}H_{11}Cl_1F_5N_1O_5[0.8H_2O]$: C, 38.45; H, 3.13; N, 3.45; Found: C, 38.45; H, 2.76; N, 3.41

Example 16

Methyl 4-isopropoxy-2,6-bis(trifluoromethyl)-3-pyridinecarboxylate

This compound was obtained by the addition of 2-iodopropane (50 ml, 0.50 mol) and potassium carbonate (16.6 g, 0.12 mol) to a solution of product of Example 4 (30.0 g, 0.10 mol) in acetone (150 ml) as described above. The crude product, an orange oil (38.91 g), was purified via HPLC (4% ethyl acetate/petroleum ether) followed by recrystallization (petroleum ether) to afford the product as a white solid (27.67 g). Yield-84%; mp 51°–52° C.

Anal. Calc'd. for $C_{12}H_{11}N_1O_3F_6$: C, 43.51; H, 3.35; N, 4.23; Found: C, 43.57; H, 3.38; N, 4.22

Example 17

Methyl 4-methoxy-2,6-bis(trifluoromethyl)-3-pyridinecarboxylate

This compound was obtained by the addition of methyl iodide (32.3 ml, 0.519 mol) and potassium carbonate (14.4 g, 0.104 mol) to a solution of product of Example 4 (25.0 g, 0.086, 5 mol) in acetone (100 ml) as described above. The crude product, a yellow solid (27.25 g), was recrystallized (chloroform-petroleum ether) to afford white rods (22.95 g), yield-88%; mp 101°–103° C.

Anal. Calc'd. for $C_{10}H_7N_1O_3F_6$: C, 39.62; H, 2.33; N, 4.62; Found: C, 39.76; H, 2.33; N, 4.62

Example 18

Methyl 4-[(diethoxyphosphinyl)oxy]-2,6-bis(trifluoromethyl)-3-pyridinecarboxylate Triethylamine (25.2 ml, 0.18 mol) was added dropwise to a cooled (0° C.) solution of diethyl phosphite (23.2 ml, 0.18 mol) and product of Example 4 (50.0 g, 0.17 mol) in carbon tetrachloride (100 ml). The reaction mixture, which had developed a heavy flocculent precipitate, was stirred at 0° C. for 30 minutes before being warmed to room temperature for an additional 24 hours. The reaction mixture was washed consecutively with 1N aq hydrochloric acid (1×250 ml), 0.5N aqueous sodium hydroxide (4×100 ml) and water (1×250 ml) before being dried (MgSO$_4$), filtered and evaporated (aspirator) to a yellow oil (61.53 g). Kugelrohr distillation (120° C. at 25 Pa) afforded the product as a very pale yellow oil (59.03 g). Yield-82%, $n_D^{25}$ 1.4197.

Anal. Calc'd. for $C_{13}H_{14}N_1O_6P_1F_6$: C, 36.72; H, 3.32; N, 3.29; Found: C, 36.64; H, 3.58; N, 3.06

Preparation of 4-Halopyridinemonocarboxylate Compounds

Compounds of Formula C are prepared as precursors for compounds having an O, S, or N atoms substituted on the pyridine ring at the 4-position. The 4-halo-substituted compounds are conveniently prepared by treatment of a 4-hydroxy pyridine compound such as, from Examples 3, 4, or 5, with a halogenating agent such as POCl$_3$ in the presence of a base. Preparation of these compounds are exemplified in the following Examples 19-22.

Example 19

Ethyl 2,6-bis(trifluoromethyl)-4-chloro-3-pyridinecarboxylate

A 500 ml round bottom flask equipped with nitrogen inlet and magnetic stirrer is charged with 40 g (0.132 mol) of product from Example 3 and 24.97 g (0.233 mol) of 2,6-lutidine. To this is slowly added (exothermic) 185 ml (1.98 mol) of phosphorus oxychloride. The flask is fitted with a condenser and the mixture is heated to reflux. After refluxing for 18 hours the material is cooled, concentrated, and the mixture was poured into 150 g of ice slowly. The ice mixture was then poured into 200 ml of 10% HCl (aqueous) and extracted twice with ether. The combined ether layers were washed with 10% NaOH (aqueous), dried (MgSO$_4$) and concentrated in vacuo affording a black oil. The residue was kugelrohr distilled at 67 Pa. The earlier fraction (pot temperature 50° C.) was discarded. The later fraction (pot temperature 85° C.) afforded 25.15 g (60%) of product, $n_D^{25}$ 1.4185.

Anal. Calc'd. for $C_{10}H_6Cl_1F_6N_1O_2$: C, 37.35; H, 1.88; N, 4.36; Found: C, 37.51; H, 1.74; N, 4.23

Example 20

Methyl 2,6-bis(trifluoromethyl)-4-chloro-3-pyridinecarboxylate

A mixture of 6.7 g (0.0232 mol) of product of Example 4, 2.8 g (0.026 mol) of 2,6-lutidine, and 50 ml of POCl$_3$ was held at reflux for 18 hours and concentrated. The residue was treated with water and extracted with ether. The ether extract was washed with 10% NaOH and then with saturated NaCl, dried, and concentrated. The residue was kugelrohr distilled at 133 Pa (pot temperature 90° C.). The distillate was recrystallized from hexane at low temperature to give 1.4 g (19.7%) of product; mp 48°-49° C.

Anal. Calc'd. for $C_9H_4Cl_1F_6N_1O_2$: C, 35.14; H, 1.31; N, 4.56; Cl, 11.53; Found: C, 35.20; H, 1.37; N, 4.55; Cl, 11.52

Example 21

Ethyl 4-chloro-6-(chlorodifluoromethyl)-2-(trifluoromethyl)-3-pyridinecarboxylate This compound was prepared as described in Example 19: 75 g (0.235 mol) of product of Example 5, 50.29 g (55 ml, 0.469 mol) of 2,6-lutidine and 252.66 g (214 ml, 2.3 mol) of phosphorus oxychloride were reacted affording 68 g of a black oil. Crude was purified by kugelrohr distillation at 200 Pa, pot temperature 110° C., to give 48 g (60%) of product as a yellow oil; $n_D^{25}$ 1.4466.

Anal. Calc'd. for $C_{10}H_6Cl_2F_5N_1O_2$: C, 35.53; H, 1.79; N, 4.14; Found: C, 35.86; H, 2.12; N, 4.16

Example 22

Methyl 4-chloro-6-(chlorodifluoromethyl)-2-(trifluoromethyl)-3-pyridinecarboxylate A mixture of 5.0 g (0.016 mol) of product of Example 5, 8.38 g (0.154 mol) of KOH, 45 ml of water in 100 ml of ethanol were refluxed for 16 hours. The reaction mixture was poured into 250 ml of water containing 50 ml of HCl, extracted with ether, dried (MgSO$_4$) and concentrated in vacuo to 3.35 g of solid. Then 45 ml of SOCl$_2$ was added to the solid and this was refluxed for 2 hours. Reaction mixture was concentrated in vacuo and 45 ml of methanol was added to the residue and refluxed for 16 hours. Reaction mixture was concentrated in vacuo. The residue was dissolved in ether, extracted with 10% K$_2$CO$_3$, and water. The combined aqueous layers were acidified with concentrated HCl, extracted with ether, dried (MgSO$_4$) and concentrated in vacuo to 2.11 g of white solid. To this solid was added 1.21 ml (0.010 mol) of 2,6-lutidine and 20 ml of POCl$_3$. This was refluxed for 16 hours. The reaction mixture was concentrated in vacuo. The residue was poured into water, extracted with ether, washed with 10% HCl, dried (MgSO$_4$) and concentrated in vacuo to 2.17 g of brown oil. Then 50 ml of MeOH was added and this was refluxed for 3½ hours and then stirred at room temperature for 72 hours. The reaction mixture was concentrated in vacuo to 1.88 g of crude produt. Kugelrohr distillaton at 47 Pa, pot temperature 80° C., afforded 1.55 g (68.3%) of product as a clear oil, $n_D^{25}$ 1.4493.

Anal. Calc'd. for $C_9H_4F_5Cl_2N_1O_2$: C, 33.36; H, 1.24; N, 4.32; Found: C, 33.53 H, 1.31; N, 4.31

Preparation of 4-Sulfur Substituted-Pyridinemonocarboxylate Compounds

The foregoing 4-halo substituted compounds of Examples 19-22 may be employed as intermediates in the preparation of substituted pyridinemonocarboxylate compounds in which the substituent atom at the 4-position on the pyridine ring is selected from O, S, and N. Pyridinemonocarboxylates according to the present invention which are substituted by a sulfur atom at the 4-position of the pyridine ring are prepared by the reaction of the corresponding 4-halo pyridine compound with a thiol in the presence of a base, as illustrated in the following Examples 23-26.

Example 23

Ethyl 2,6-bis(trifluoromethyl)-4-phenylthio-3-pyridinecarboxylate

To a mixture of 1.70 g (0.025 mol) of sodium ethoxide in 100 ml ethanol was added 2.74 g (0.025 mol) of thiophenol followed by 5.3 g (0.016 mol) of product of Example 19. The reaction mixture was held at reflux for 2 days and filtered. The filtrate was poured into water and extracted into ether. The ether extract was washed with 10% NaOH, dried (MgSO$_4$) had concentrated to give 4.14 g (63.6%) of product as a solid; mp 58°–61° C.

Anal. Calc'd. for $C_{16}H_{11}F_6N_1O_2S_1$: C, 48.61; H, 2.80; N, 3.54; Found: C, 48.75; H, 2.77; N, 3.50

Example 24

Ethyl 2,6-bis(trifluoromethyl)-4-phenylsulfonyl-3-pyridinecarboxylate

To a 7° C. solution of 3.14 g (0.008 mol) of product of Example 23 in 70 ml of methylene chloride was added 3.77 g (0.022 mol) of m-chloroperbenzoic acid (MCPBA). The reaction mixture was stirred at 7° C. for 1 hour and then at room temperature for 18 hours. The reaction mixture was washed with saturated sodium bicarbonate, dried (MgSO$_4$) and concentrated. The residue was purified by HPLC using 5% ethyl acetate/cyclohexane as eluant to give 1.94 g (57.2%) of product as a solid; mp 48°–50° C.

Anal. Calc'd. for $C_{16}H_{11}F_6N_1O_4S_1$: C, 44.97; H, 2.60; N, 3.28; Found: C, 44.95; H, 2.50; N, 3.34

Example 25

Ethyl 4-ethylthio-2,6-bis(trifluoromethyl)-3-pyridinecarboxylate

A mixture of 3.0 g (0.009 mol) of product of Example 19, 1.55 g (0.011 mol) of K$_2$CO$_3$ and 3.5 ml (0.047 mol) of ethanethiol in 15 ml of methyl isobutyl ketone was stirred at reflux for 60 hours. The reaction mixture was concentrated. The residue was taken up in ether, washed with 10% NaOH and water, dried (MgSO$_4$) and concentrated in vacuo to 2.98 g of dark oil which was purified by HPLC using 5% ethyl acetate/cyclohexane as eluting solvent affording 2.18 g (69.8%) of product as a tan solid; mp 36°–37.5° C.

Anal. Calc'd. for $C_{12}H_{11}F_6N_1O_2S_1$: C, 41.50; H, 3.19; N, 4.03; Found: C, 41.45; H, 3.22; N, 4.01

Example 26

Ethyl 2,6-bis(trifluoromethyl)-4-ethylsulfinyl-3-pyridinecarboxylate

Ethanethiol (5.33 ml, 0.072 mol) followed by 14.72 g (0.046 mol) of product of Example 19 was added to a solution of sodium ethoxide prepared from 1.66 g (0.072 mol) of sodium in 100 ml of ethanol and stirred at reflux overnight. The reaction mixture was filtered, poured into 200 ml of water, extracted with ether, washed with 10% NaOH, dried (MgSO$_4$) and concentrated in vacuo to 9.45 g of yellow oil. This oil in 150 ml of CH$_2$Cl$_2$ was cooled to 5° C. and 3.73 g (0.022 mol) of MCPBA was added. Reaction was monitored by TLC. The reaction mixture was filtered, washed with NaHCO$_3$, dried (MgSO$_4$) and concentrated in vacuo to give 5.06 g of yellow oil. This was purified by HPLC using 10% ethyl acetate/cyclohexane as eluting solvent to give 3.81 g (65.6%) of an oil. A portion (1.71 g) of this oil was kugelhohr distilled at 22 Pa, pot temperature 95° C., affording 1.45 g of product as a clear oil, $n_D^{25}$ 1.4575.

Anal. Calc'd. for $C_{12}H_{11}F_6N_1O_3S_1$: C, 39.68; H, 3.05; N, 3.86; Found: C, 39.72; H, 3.03; N, 3.85

Preparation of 4-Nitrogen-Substituted Pyridine Compounds

As was stated earlier, the 4-halo-substituted compounds of this invention are employed as intermediates in the preparation of compounds of this invention which have an O, S, or N atom as the first substituent atom off of the pyridine ring at the 4-position. Preparation of 4-amino and 4-azido-substituted compounds are shown in the following Examples 27–30.

Example 27

Ethyl 4-azido-2,6-bis(trifluoromethyl)-3-pyridinecarboxylate

A mixture of 5.0 g (0.0155 mol) of product of Example 19, 1.0 g (0.0154 mol) of sodium azide and 20 ml of DMF was stirred for 1 hour and poured into 100 ml of water. The organic was extracted into 100 ml of CH$_2$Cl$_2$ which was washed with 50 ml of water and concentrated. The residue (6.0 g) was dissolved in 50 ml of petroleum ether then washed with 50 ml of water twice, dried (MgSO$_4$) and concentrated to give a solid which was recrystallized from petroluem ether at low temperature to give 4.2 g (82%) of product as a light yellow solid; mp 63°–64.5° C.

Anal. Calc'd. for $C_{10}H_6F_6N_4O_2$: C, 36.60; H, 1.84; N, 17.07; Found: C, 36.60; H, 1.86; N, 17.03

Example 28

Ethyl 4-amino-2,6-bis(trifluoromethyl)-3-pyridinecarboxylate

A mixture of 2.0 g (0.00611 mol) of product of Example 27, 100 mg of 10% Pd-C and 20 ml of ethanol was hydrogenated with 30 lbs. hydrogen pressure for three hours and filtered. The filtrate was concentrated. The residual oil (1.7 g) was triturated with petroleum ether and filtered to give 1.5 g (87%) of product as a white powder; mp 43°–45° C.

Anal. Calc'd. for $C_{10}H_8F_6N_2O_2$: C, 39.75; H, 2.67; N, 9.27; Found: C, 39.78; H, 2.70; N, 9.24

Example 29

Ethyl 4-(diethylamino)-2,6-bis(trifluoromethyl)-3-pyridinecarboxylate (0.2 hydrate)

Diethylamine (2.1 ml, 0.020 mol) was slowly added to a solution of 3.0 g (0.009 mol) of product of Example 19 in 15 ml of DMF and stirred overnight. Reaction mixture was poured into water, extracted with ether, washed with water, dried (MgSO$_4$) and concentrated. The residue was kugelrohr distilled twice at 28 Pa, pot temperature 76° C., to afford 2.06 g (63.2%) of product as a yellow oil, $n_D^{25}$ 1.4593.

Anal. Calc'd. for $C_{14}H_{16}F_6N_2O_2[0.2H_2O]$: C, 46.46; H, 4.57; N, 7.74; Found: C, 46.48; H, 4.48; N, 7.77

Example 30

Ethyl 4-(dimethylamino)-2,6-bis(trifluoromethyl)-3-pyridinecarboxylate

A mixture of 7.67 g (0.024 mol) of product of Example 19 and 5.4 g (0.048 mol) of 40% solution of dimethylamine in $H_2O$ and 50 ml of DMF was stirred for three hours. The temperature rose to 48° C. and dropped back down to room temperature. The reaction mixture was poured into $H_2O$, extracted with ether, washed with diluted HCl, dried ($MgSO_4$) and concentrated in vacuo to 6.63 g of solid which was recrystallized in hot hexane affording 6.01 g (75.8%) of product as a white solid; mp 63.5°–65° C.

Anal. Calc'd. for $C_{12}H_{12}F_6N_2O_2$: C, 43.65; H, 3.66; N, 8.48; Found: C, 43.73; H, 3.72; N, 8.45

Preparation of Further 4-Oxygen Substituted Compounds

As was stated above, 4-alkoxy compounds of the present invention may be prepared by alkylation of the corresponding 4-hydroxypyridine compound. Where the desired substituent at the 4-position on the pyridine ring is more complex than a simple alkoxy substituent, it may be desirable to prepare the compound by proceeding via the intermediate 4-halo-substituted compound. Examples 31–33 illustrate this procedure.

Example 31

Ethyl 2,6-bis(trifluoromethyl)-4-{4-[(1-ethoxycarbonyl)ethoxy]phenoxy}-3-pyridinecarboxylate A 250 ml round bottom flask is charged with 3.54 g (0.011 mol) of product of Example 19, 2.31 g (0.011 mol) of 4-[(1-ethoxycarbonyl)ethoxy]phenol and 1.82 g (0.013 mol) of $K_2CO_3$ in 150 ml of methyl isobutyl ketone. This mixture was stirred at reflux for 18 hours, filtered and concentrated. The residue was taken up in ether, washed with 5% NaOH, water, dried ($MgSO_4$) and concentrated in vacuo to afford 3.75 g of an orange oil. Purification by HPLC using 18% ethyl acetate/cyclohexane as eluting solvent gave 2.66 g of an oil which was kugelrohr distilled at 41 Pa, pot temperature 150°–154° C., affording 2.56 g (47.0%) of product as a clear oil, $n_D^{25}$ 1.4732.

Anal. Calc'd. for $C_{21}H_{19}F_6N_1O_6$: C, 50.92; H, 3.87; N, 2.83; Found: C, 51.00; H, 3.89; N, 2.77

Example 32

Ethyl 4-(3-methyl-4-nitrophenoxy)-2,6-bis(trifluoromethyl)-3-pyridinecarboxylate This product was prepared as described in Example 31: 7.0 g (0.022 mol) of product of Example 19, 3.31 g (0.024 mol) of $K_2CO_3$, 3.33 g (0.022 mol) of 3-methyl-4-nitrophenol in 75 ml of methyl isobutyl ketone were reacted affording 9.18 g of an oil. Purification by HPLC using 5% ethyl acetate/cyclohexane as eluting solvent gave 5.31 g (55.1%) of product as a yellow solid; mp 55°–57° C.

Anal. Calc'd. for $C_{17}H_{12}F_6N_2O_5$: C, 46.59; H, 2.76; N, 6.39; Found: C, 46.52; H, 3.00; N, 6.35

Example 33

Ethyl 4-(4-nitrophenoxy)-2,6-bis(trifluoromethyl)-3-pyridinecarboxylate

A mixture of 7.0 g (0.022 mol) of product of Example 19, 3.03 g (0.022 mol) of p-nitrophenol and 3.31 g (0.024 mol) of $K_2CO_3$ in 75 ml of methyl isobutyl ketone was refluxed for 17 hours. The cooled reaction mixture was concentrated in vacuo. The residue was dissolved in ether, washed with $H_2O$, dried ($MgSO_4$) and concentrated in vacuo. The residue was recrystallized in hot hexane to give 5.09 g of tan solid. The solid was purified by HPLC using 3% ethyl acetate/cyclohexane as eluting solvent affording 3.88 g (41.6%) of product as a white solid; mp 111.5°–113.5° C.

Anal. Calc'd. for $C_{16}H_{10}F_6N_2O_5$: C, 45.30; H, 2.38; N, 6.60; Found: C, 45.37; H, 2.65; N, 6.59

Preparation of 5-Alkyl Substituted Pyridine Compounds

Preparations of pyridinemonocarboxylate compounds of this invention which are substituted with a lower alkyl group at the 5-position are exemplified in the following Examples 34–72.

Example 34

Ethyl 3-amino-2-propionyl-4,4,4-trifluorocrotonate

To a mechanically stirred solution of 287 g (1.99 mol) of ethyl propionylacetate in 500 ml of dry DME was added under nitrogen 8.6 g (0.348 mol) of freshly cut sodium. After all sodium had dissolved, 256 g (2.69 mol) of trifluoroacetonitrile was added over a 35 hour period. The reaction mixture was concentrated. The residue was washed with water and extracted into 500 ml of ether. The ether solution was dried and concentrated. The residue was kugelrohr distilled at 67 Pa. and then was redistilled at 67 Pa through a spinning band column. The first fraction (bp 40°–78° C.) was discarded. The next fraction (bp 79°–82° C.) was 151 g (31.6%) of product, $n_D^{25}$ 1.4574.

Anal. Calc'd. for $C_9H_{12}F_3N_1O_3$: C, 45.19; H, 5.06; N, 5.86; Found: C, 45.19; H, 5.05; N, 5.83

EXAMPLE 35

Ethyl 2,6-bis(trifluoromethyl)-4-hydroxy-5-methyl-3-pyridinecarboxylate

To a cold (−78° C.) solution of LDA, from 0.2 mol of n-BuLi, 29 ml (0.207 mol) of diisopropylamine and 200 ml of dimethoxyethane was added a solution of 23.4 g (0.1 mol) of product of Example 34 in 500 ml of dimethoxyethane in 5 minutes. The reaction mixture turned red and precipitate formed and made magnetic stirring difficult. The reaction flask was shaken by hand for 5 minutes and the reaction mixture was treated with 25 ml (0.2 mol) of ethyl trifluoroacetate at once. The precipitate gradually dissolved. The reaction mixture was stirred and warmed to room temperature in 2 hours, then was poured into 500 ml of ice water. The mixture was extracted with ether. The aqueous layer was acidified with concentrated HCl to give a white solid. The ether layer was extracted with 10% $K_2CO_3$ (200 ml) and the basic extract was acidified with concentrated HCl to give additional solid. The combined solid was dissolved in 10% $K_2CO_3$ and washed with ether. The aqueous solution was acidified with concentrated HCl and filtered. The solid was recrystallized from chloroform-acetone to remove 8.0 g of a solid. The mother liquor was concentrated and the residue was kugelrohr distilled at 133 Pa (pot temperature 120° C.) to give an oil-solid mixture which was crystallized from hexane at low temperature to give 4.8 g (15%) of product; mp 23°–24.5° C. This material melted upon standing, $n_D{}^{25}$ 1.4343.

Anal. Calc'd. for $C_{11}H_9F_6N_1O_3$: C, 41.65; H, 2.88; N, 4.42; Found: C, 41.47; H, 2.93; N, 4.38

EXAMPLE 36
Ethyl 2,6-bis(trifluoromethyl)-4-ethoxy-5-methyl-3-pyridinecarboxylate A mixture of 7.8 g (0.0246 mol) of product of Example 35, 3.5 g of $K_2CO_3$, 20 g of iodoethane, and 100 ml of acetone was held at reflux for 2 days and concentrated. The reaction mixture was treated with 150 ml of water and extracted with 200 ml of ether. The ether extract was dried and concentrated. The residual solid (7.5 g) was recrystallized from hexane at low temperature to give 6.6 g (77.7%) of product; mp 72.5°–74° C.

Anal. Calc'd. for $C_{13}H_{13}F_6N_1O_3$: C, 45.23; H, 3.78; N, 4.06; Found: C, 45.32; H, 3.81; N, 4.05

EXAMPLE 37
Ethyl 2,6-bis(trifluoromethyl)-4-isopropoxy-5-methyl-3-pyridinecarboxylate A mixture of 15.1 g (0.209 mol) of product of Example 35, 6.6 g (0.2 mol) of potassium carbonate, 32 g of isopropyl iodide and 50 ml of acetone was held at reflux for 18 hours and concentrated. The residue was treated with water and filtered. The solid was dissolved in ether (100 ml) and the ether solution was washed with 50 ml of 10% NaOH, dried, and concentrated. The residue was recrystallized from hexane to give 14.2 g (83%) of product; mp 53°–55° C.

Anal. Calc'd. for $C_{14}H_{15}F_6N_1O_3$: C, 46.80; H, 4.21; N, 3.90; Found: C, 46.76; H, 4.21; N, 3.91

EXAMPLE 38
Ethyl 5-methyl-4-(2-propenyloxy)-2,6-bis(trifluoromethyl)-3-pyridinecarboxylate To a mixture of 10 g (0.03 mol) of product of Example 35 with 9.7 g (0.07 mol) of $K_2CO_3$ in 100 ml of DMF was charged 8 g (0.07 mol) of allyl bromide. The resulting mixture was stirred at 25° C. for 4 days. The reaction mixture was poured into $H_2O$, and extracted with duethyl ether. The ether phase was dried (MgSO4), and concentrated in vacuo to 10.2 g (95%) of product as a yellow oil: $n_D{}^{25}$ 1.4334

Anal. Calc'd. for $C_{14}H_{13}F_6N_1O_3$: C, 47.07; H, 3.67; N, 3.92; Found: C, 47.24; H, 3.70; N, 3.92

EXAMPLE 39
2,6-Bis(trifluoromethyl)-4-hydroxy-5-methyl-3-pyridinecarboxylic acid A mixture of 13 g (0.041 mol) of product of Example 35, 10 g of KOH, 100 ml of methanol, 100 ml of water was held at reflux for 20 hours, cooled, and poured into ice water (500 ml) containing 20 ml of concentrated HCl. The mixture was extracted with ether. The ether solution was dried and concentrated to give a solid which was recrystallized from hexane to give 4.68 g (39%) of product; mp 161°–162° C. A second crop, 4.74 g (40%), mp 155°–159° C., was obtained from mother liquor. Total yield was 79%.

Anal. Calc'd. for $C_9H_5F_6N_1O_3$: C, 37.38; H, 1.74; N, 4.84; Found: C, 37.31; H, 1.78; N, 4.84

EXAMPLE 40
Ethyl 2,6-bis(trifluoromethyl)-4-acetoxy-5-methyl-3-pyridinecarboxylate A mixture of 1.26 g (0.016 mol) of pyridine, 1.61 g (0.016 mol) of acetic anhydride and 5.0 g (0.016 mol) of product of Example 35 in 50 ml of ether was stirred for 3 hours and filtered. The filtrate was concentrated in vacuo to give 5.38 g (95%) of product as a solid; mp 49°–51° C.

Anal. Calc'd. for $C_{13}H_{11}F_6N_1O_4$: C, 43.47; H, 3.09; Found: C, 43.42; H, 3.13

Further derivatives of the compound of Example 35 were prepared as in Example 40 are shown in the following Table I. These compounds were purified by one of the following procedures A and B, and the purification method is indicated in the table. An equimolar mixture of product of Example 35, the appropriate acid chloride or acid anhydride and pyridine in ether was stirred for several hours and filtered. The filtrate was concentrated to give the desired product which could be purified by recrystallization from appropriate solvent (procedure A). In case of incomplete reaction between the starting compound and acid chloride, the ether filtrate was washed successively with diluted HCl, 10% $K_2CO_3$ and water, then was dried (MgSO4) and concentrated to give the desired product which could then be purified by recrystallization from an appropriate solvent (procedure B).

TABLE 1

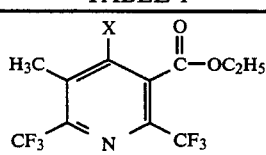

| Example | X | Starting Material | Purification Method | M.P. | Element | Calculated | Found |
|---|---|---|---|---|---|---|---|
| 41 | [(1,1-dimethylethyl)-carbonyl]-oxy | trimethylacetyl chloride | B | 34–36° C. | C | 47.89 | 47.77 |
|  |  |  |  |  | H | 4.27 | 4.31 |
| 42 | (4-methylphenyl) sulfonyloxy | p-toluenesulfonyl chloride | A | 85–87° C. | C | 45.87 | 45.85 |
|  |  |  |  |  | H | 3.21 | 3.21 |
| 43 | benzoyloxy | benzoyl chloride | A | 48–50° C. | C | 51.32 | 51.28 |
|  |  |  |  |  | H | 3.11 | 3.15 |
| 44 | 3-(trifluoromethyl)- | m-trifluoromethyl- | A | 89–91° C. | C | 46.64 | 46.88 |

TABLE 1-continued

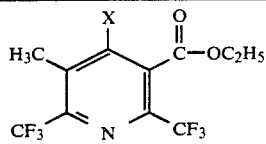

| Example | X | Starting Material | Purification Method | M.P. | Element | Calculated | Found |
|---|---|---|---|---|---|---|---|
| | benzoyloxy | benzoyl chloride | | | H | 2.47 | 2.60 |
| 45 | 2,4-dichloro-benzoyloxy | 2,4-dichlorobenzoyl chloride | A | 87–89° C. | C | 44.10 | 44.19 |
| | | | | | H | 2.26 | 2.27 |
| 46 | 2-chlorobenzoyloxy | o-chlorobenzoyl chloride | A | 64–66° C. | C | 47.44 | 47.49 |
| | | | | | H | 2.65 | 2.70 |
| | | | | | Cl | 7.78 | 7.77 |
| 47 | chloroacetoxy | chloroacetyl chloride | A | ($n_D^{25}$ 1.4407) | C | 39.66 | 39.70 |
| | | | | | H | 2.56 | 2.56 |
| | | | | | Cl | 9.00 | 8.98 |
| 48 | 2,6-dichloro-benzoyloxy | 2,6-dichlorobenzoyl chloride | A | 90–92° C. | C | 44.10 | 44.18 |
| | | | | | H | 2.26 | 2.27 |
| | | | | | Cl | 14.46 | 14.38 |
| 49 | 4-methoxy-benzoyloxy | p-anisoyl chloride | A | 68–70° C. | C | 50.56 | 50.77 |
| | | | | | H | 3.35 | 3.42 |
| 50 | 4-nitrobenzoyloxy | p-nitrobenzoyl-chloride | B | 104–106° C. | C | 46.37 | 46.37 |
| | | | | | H | 2.59 | 2.63 |
| | | | | | N | 6.01 | 5.99 |
| 51 | pentafluoroben-zoyloxy | pentafluorobenzoyl chloride | B | ($n_D^{25}$ 1.4472) | C | 42.29 | 42.15 |
| | | | | | H | 1.58 | 1.50 |
| | | | | | F | 40.88 | 41.04 |
| 52 | phenylacetoxy | phenylacetyl chloride | B | ($n_D^{25}$ 1.4726) | C | 52.42 | 52.53 |
| | | | | | H | 3.47 | 3.55 |
| 53 | 2-methylbenzoyloxy | o-toluoyl chloride | B | 32–34° C. | C | 52.42 | 52.39 |
| | | | | | H | 3.47 | 3.47 |
| 54 | (4-chlorophenoxy)-acetoxy | p-chlorophenoxy-acetyl chloride | B | 63–66° C. | C | 46.98 | 47.51 |
| | | | | | H | 2.90 | 3.00 |
| | | | | | Cl | 7.30 | 8.15 |
| 55 | (4-chlorophenyl)-acetoxy | p-chlorophenyl-acetyl chloride | A | 83–85° C. | C | 48.58 | 48.58 |
| | | | | | H | 3.00 | 3.02 |
| | | | | | Cl | 7.55 | 7.53 |
| 56 | (3-trifluoro-methyl)phenyl-acetoxy | m-trifluoromethyl-phenylacetyl chloride | A | 53–55° C. | C | 47.73 | 47.71 |
| | | | | | H | 2.80 | 2.68 |
| | | | | | N | 2.78 | 2.74 |
| 57 | (2,4-dichlorophenyl)-acetoxy | 2,4-dichloro-phenylacetyl chloride | A | 75–77° C. | C | 45.26 | 45.23 |
| | | | | | H | 2.60 | 2.38 |
| | | | | | N | 2.78 | 2.76 |
| 58 | (4-trifluoro-methoxy)-ben-zoyloxy | 4-trifluoromethoxy-benzoyl fluoride | B | 61–63° C. | C | 45.16 | 44.32 |
| | | | | | H | 2.39 | 2.31 |
| | | | | | N | 2.77 | 2.82 |
| 59 | 4-chlorobenzoyloxy | p-chlorobenzoyl chloride | A | 76–78° C. | C | 47.44 | 47.03 |
| | | | | | H | 2.65 | 2.47 |
| | | | | | N | 3.07 | 3.09 |
| 60 | 4-methylbenzoyloxy | p-toluoyl chloride | B | 66–68° C. | C | 52.42 | 52.57 |
| | | | | | H | 3.47 | 3.33 |
| | | | | | N | 3.22 | 3.23 |
| 61 | (4-trifluoromethyl)-benzoyloxy | p-trifluoromethyl-benzoyl chloride | B | 67–69° C. | C | 46.64 | 46.20 |
| | | | | | H | 2.47 | 2.27 |
| | | | | | N | 2.86 | 3.18 |
| 62 | (2,4-dichloro-phenoxy)-acetoxy | 2,4-dichlorophenoxy-acetyl chloride | B | 97–98° C. | C | 43.87 | 43.81 |
| | | | | | H | 2.52 | 2.39 |
| | | | | | N | 2.69 | 2.68 |

EXAMPLE 63
Ethyl 2,6-bis(trifluoromethyl)-4-[(ethoxycarbonyl)methoxy]-5-methyl-3-pyridinecarboxylate A mixture of 5.0 g (0.016 mol) of product of Example 35, 3.95 g (0.024 mol) of ethyl bromoacetate, 2.18 g (0.016 mol) of $K_2CO_3$ and 75 ml of acetone was held at reflux for 18 hours and filtered. The filtrate was concentrated. The residue was stirred with toluene and filtered. The toluene filtrate was concentrated to give 4.46 g (70.2%) of product as a solid; mp 42°–44° C.

Anal. Calc'd. for $C_{15}H_{15}F_6N_1O_5$: C, 44.68; H, 3.75; Found: C, 44.67; H, 3.76

EXAMPLE 64
Ethyl 2,6-bis(trifluoromethyl)-4-[(phenylcarbonyl)methoxy]-5-methyl-3-pyridinecarboxylate Reaction of product of Example 35 with bromoacetophenone and potassium carbonate similar to the above Example 63 gave a crude product which was recrystallized successively from methanol and cyclohexane to give 4.45 g (65.4%) of product as a solid; mp 95°–97° C.

Anal. Calc'd. for $C_{19}H_{15}F_6N_1O_4$: C, 52.42; H, 3.47 Found: C, 52.97; H, 3.41

EXAMPLE 65

Ethyl 2,6-bis(trifluoromethyl)-4-chloro-5-methyl-3-pyridinecarboxylate

A mixture of 5.0 g (0.016 mol) of product of Example 35, 4.52 g (0.0362 mol) of 2,6-lutidine and 34 ml of phosphorus oxychloride was held at reflux for 20 hours and concentrated in vacuo. The residue was quenched with water and extracted with ether. The ether extract was washed successively with 10% $K_2CO_3$ and water, dried ($CaSO_4$) and concentrated in vacuo to give 3.06 g (57.8%) of product as a brown oil, $n_D^{25}$ 1.4313.

Anal. Calc'd. for $C_{11}H_8Cl_1F_6N_1O_2$: C, 39.36; H, 2.40; Cl, 10.56; Found: C, 39.15; H, 2.35; Cl, 10.47

EXAMPLE 66

Ethyl 6-(chlorodifluoromethyl)-4-hydroxy-5-methyl-2-(trifluoromethyl)-3-pyridinecarboxylate To 85 ml of dry ether and 21.4 ml (0.152 mol) of diisopropylamine at $-78°$ C. was added 97 ml (0.150 mol) of 1.55M n-BuLi. After stirring at $-78°$ C. for 20 minutes a solution of 16.3 g (0.068 mol) of product of Example 34 in 10 ml of dry ether was added. After stirring at $-78°$ C. for 1 hour, 35 g (0.221 mol) of ethyl chlorodifluoroacetate was added. Stirring at $-78°$ C. was continued for 1 hour and then warmed to room temperature in 1½ hour. The reaction mixture was poured into 200 ml of ice water and extracted with ether. The ether was extracted with 15% $K_2CO_3$ and water. The water extracts were combined, acidified with concentrated HCl and extracted with ether. The original aqueous layer was acidified with concentrated HCl, extracted with ether and combined with the above ether extract, dried ($MgSO_4$) and concentrated in vacuo affording 17.7 g of solid. This solid was heated on the kugelrohr apparatus at 125° C. for ½ hour at atm. pressure and then distilled at 19 Pa, pot temperature 69° C. to give 13.57 g (59.8%) of product as a white solid; mp 37°–39° C.

Anal. Calc'd. for $C_{11}H_9Cl_1F_5N_1O_3$: C, 39.60; H, 2.72; N, 4.20; Found: C, 39.61; H, 2.71; N, 4.19

EXAMPLE 67

Ethyl 6-(difluoromethyl)-4-hydroxy-5-methyl-2-(trifluoromethyl)-3-pyridinecarboxylate (0.4 hydrate)

The product from Example 66 above (11.52 g, 0.0345 mol), 6.98 g (0.069 mol) of triethylamine and 0.58 g of Pd-C (10%) in 125 ml of ethanol was hydrogenated at 40° C. under 522 kPa $H_2$ pressure for 18 hours. The reaction mixture was filtered through Celite and concentrated. The residue was taken up in ether, washed with 10% HCl, dried ($MgSO_4$) and concentrated in vacuo at 8.86 g of orange oil. Kugelrohr distillation at 53 Pa, pot temperature 62°–79° C., yielded 6.20 g of yellow solid which was purified by HPLC using 5% ethyl acetate/cyclohexane as eluting solvent affording 3.74 g (35.4%) of product as a white solid; mp. 35°–38° C.

Anal. Calc'd. for $C_{11}H_{10}F_5N_1O_3$ [$0.4H_2O$]: C, 43.12; H, 3.55; N, 4.57; Found: C, 43.26; H, 3.26; N, 4.61

EXAMPLE 68

Ethyl 6-(difluoromethyl)-4-(4-methoxybenzoyloxy)-5-methyl-2-(trifluoromethyl)-3-pyridinecarboxylate The product from Example 67 above (1.59 g, 0.005 mol), 0.91 g (0.005 mol) of p-anisoyl chloride, and 0.42 g (0.005 mol) of pyridine in 25 ml of ether was stirred at room temperature for 30 minutes. The reaction mixture was filtered, washed with diluted HCl, washed with 15% $K_2CO_3$, dried ($MgSO_4$) and concentrated in vacuo affording 1.79 g of solid which was recrystallized in hot hexane-ether to give 1.46 g (67.4%) of product as a white solid; mp 63°–65° C.

Anal. Calc'd. for $C_{19}H_{16}F_5N_1O_5$: C, 52.66; H, 3.72; N, 3.23; Found: C, 52.89; H, 3.70; N, 3.12

EXAMPLE 69

Ethyl 2-butyryl-3-amino-4,4,4-trifluoro-2-butenoate

To a mechanically stirred mixture of 100 g (0.632 mol) of ethyl butyrylacetate, 52 g of sodium acetate, 100 ml of ethanol and 100 ml of water at 70° C. was passed 63 g of trifluoroacetonitrile in 1 day. The reaction mixture was poured into ice water. The oil precipitate was extracted into ether. The ether solution was dried and concentrated. The residue was kugelrohr distilled at 133 Pa (pot temperature 70°–110° C.). The distillate was further distilled through a Vigreaux column at 106 Pa to give 90.9 g (36.3%) of product, bp 90°–97° C., $n_D^{25}$ 1.4585.

Anal. Calc'd. for $C_{10}H_{14}F_3N_1O_3$: C, 47.43; H, 5.57; N, 5.53; Found: C, 47.45; H, 5.57; N, 5.50

EXAMPLE 70

Ethyl 2,6-bis(trifluoromethyl)-5-ethyl-4-hydroxy-3-pyridinecarboxylate

To a cold ($-78°$ C.) solution of LDA, from 0.3 mol of n-BuLi, 0.3 mol (42 ml) of diisopropylamine, and 250 ml of ether was added a solution of 38.0 g (0.150 mol) of product of Example 69 in 50 ml of ether. The reaction mixture turned red and precipitate formed. The reaction mixture was stirred at $-78°$ C. for 40 minutes, then was treated with 36 ml of ethyl trifluoroacetate. The reaction mixture was warmed to room temperature and poured into 500 ml of ice water. The aqueous layer was separated and the organic layer was extracted with 10% NaOH. The combined aqueous solution was made acidic with 50 ml of concentrated HCl. The oil precipitate was extracted into ether (500 ml). The ether extract was extracted with 200 ml of 20% $K_2CO_3$. The $K_2CO_3$ extract was acidified and the precipitate was collected and recrystallized from chloroform-acetone to remove 4.4 g of solid.

The ether solution was further extracted with 10% NaOH (200 ml). The NaOH extract was acidified to give 8 g of solid. This solid was combined with the concentrate from previous chloroform-acetone mother liquor and heated in a kugelrohr pot at 155°–160° C. for 1 hour. The distillate and the residue were combined and dissolved in ether. The ether solution was dried and concentrated and the residue was kugelrohr distilled at 67 Pa. After removal of forerun (pot temperature 40° C.), a fraction pot (pot temperature 80° C.) containing 11.5 g of a solid-oil mixture was obtained. This mixture was crystallized from hexane at low temperature to give the desired product as a solid which turned into an oil (7.4 g, 14.9%) upon standing, $n_D^{25}$ 1.4383.

Anal. Calc'd. for $C_{12}H_{11}F_6N_1O_3$: C, 43.51; H, 3.35; N, 4.23; Found: C, 43.60; H, 3.36; N, 4.22

EXAMPLE 71

Ethyl 4-hydroxy-5-methyl-6-(pentafluoroethyl)-2-(trifluoromethyl)-3-pyridinecarboxylate To a −78° C. solution of LDA (0.10 mol), prepared from 0.10 mol of n-BuLi and 14 ml (0.10 mol) of diisopropylamine in 70 ml ether was added a solution of 10.0 g (0.042 mol) of product of Example 34 in 20 ml of ether slowly to maintain a temperature below −60° C. After stirring for 30 minutes, the reaction mixture was treated with 21 ml (0.042 mol) of ethyl pentafluoropropionate. After stirring at −78° C. for 15 minutes, the reaction mixture was warmed to 10° C. in 0.5 hour and poured into 100 ml of water, and extracted with ether. The ether extract was extracted with 10% $K_2CO_3$. The combined aqueous layer and $K_2CO_3$ extract was acidified with concentrated HCl to give 4.73 g (29.5%) of beige solid; mp 115°–117° C. (dec). A 2.73 g (0.00709 mol) of the solid was heated in a kugelrohr pot at 130° C. for 0.5 hour. The distillate and residue were combined and dissolved in ether. The ether solution was dried ($CaSO_4$) and concentrated to give 2.0 g (76.9%) of product as a solid; mp 36°–38° C.

Anal. Calc'd. for $C_{12}H_9F_8N_1O_3$: C, 39.25; H, 2.47; Found: C, 38.89; H, 2.49

SALTS OF PYRIDINE MONOCARBOXYLATES

The following Examples 72–76 show the preparation of salts of the product of Example 35. An equimolar mixture of the starting material and an inorganic or organic base in an appropriate solvent was stirred for 5 minutes and concentrated in vacuo to give the salt directly or it may be purified by crystallization from an appropriate solvent.

EXAMPLE 72

Sodium Salt

A mixture of 5.0 g (0.016 mol) of product of Example 35, 1.09 g (0.016 mol) of sodium ethoxide and 50 ml of ethanol was stirred for 5 minutes and concentrated. The residue was crystallized from toluene to give 2.39 g (44.7%) of product as a light yellow solid; mp>300° C.

Anal. Calc'd. for $C_{11}H_8F_6N_1Na_1O_3$: C, 38.95; H, 2.38; Found: C, 39.08; H, 2.75

EXAMPLE 73

Diisopropylamine Salt

A mixture of 5.0 g (0.016 mol) of starting material, 2.2 ml (0.016 mol) of diisopropylamine and 50 ml of ether was stirred for 5 minutes and concentrated. The residue crystallized upon standing to give 6.26 g (94.8%) of solid; mp 85°–87° C.

Anal. Calc'd. for $C_{17}H_{24}F_6N_2O_3$: C, 48.80; H, 5.78; Found: C, 48.77; H, 5.80

EXAMPLE 74

Diethanolamine Salt

This material was prepared from 5.0 g (0.016 mol) of starting material and 1.68 g (0.016 mol) of diethanolamine by a procedure similar to Example 73 to give 2.06 g (30.9%) of beige solid; mp 101°–103° C. (toluene).

Anal. Calc'd. for $C_{15}H_{20}F_6N_2O_5$: C, 42.66; H, 4.77; Found: C, 42.70; H, 4.81

EXAMPLE 75

75% Triethylamine Salt in 25% Starting Material

This material was prepared from 5.0 g (0.016 mol) of starting material and 1.6 g (0.016 mol) of triethylamine by a procedure similar to Example 73 to give 5.78 g (87.6%) of light brown oil, $n_D^{25}$ 1.4592.

Anal. Calc'd. for $C_{11}H_9F_6N_1O_3 \cdot 3/4 C_6H_{15}N_1$: C, 47.36; H, 5.19; Found: C, 47.47; H, 5.07

EXAMPLE 76

Isopropylamine Salt

This material was prepared from 5.0 g (0.016 mol) of starting material and 0.95 g (0.016 mol) of isopropylamine by a procedure similar to Example 73 to give 2.06 g (50.0%) of a gummy brown oil which solidified upon standing; mp 95°–100° C.

Anal. Calc'd. for $C_{14}H_{18}F_6N_2O_3$: C, 44.69; H, 4.82; Found: C, 44.39; H, 4.54

Using procedures similar to those set out in detail above, further compounds were prepared and are shown in the following Table II. As used in Table II, the following abbreviations have the meanings as defined below:

Me—Methyl
Et—Ethyl
Pr—Propyl
iPr—Isopropyl
CyPr—Cyclopropyl
tBu—Tertiary butyl
CyHx—Cyclohexyl
Ph—Phenyl

TABLE II

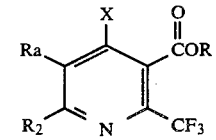

| Example | $R_2$ | Ra | X | R | mp | $n_D^{25}$ |
|---|---|---|---|---|---|---|
| 77 | $CF_3$ | Me | OH | Me | 34–36 | |
| 78 | $CF_3$ | Me | $\underset{OCPh}{\overset{O}{\underset{\|}{\|}}}$ | Me | 97–99 | |
| 79 | $CF_3$ | Me | $O^{\ominus}\overset{\oplus}{N}H_2(iPr)_2$ | Me | 87–89 | |
| 80 | $CF_2Cl$ | H | $O^{\ominus}\overset{\oplus}{N}H_2(iPr)_2$ | Me | 93–97 | |
| 81 | $CF_3$ | H | $\underset{OCN(Me)_2}{\overset{S}{\|}}$ | Me | 76–79 | |
| 82 | $CF_3$ | H | $\underset{OCN(iPr)_2}{\overset{O}{\|}}$ | Me | 59–61 | |
| 83 | $CF_3$ | H | $\underset{OCN(Me)Ph}{\overset{O}{\|}}$ | Me | 60–63 | |
| 84 | $CF_3$ | H | $\underset{OCN(Et)_2}{\overset{O}{\|}}$ | Me | 47–49 | |

TABLE II-continued $$\underset{R_2}{\overset{Ra}{\diagdown}}\underset{N}{\diagup}\overset{X}{\diagdown}\underset{CF_3}{\diagup}\overset{O}{\underset{\parallel}{C}}OR$$

| Example | $R_2$ | Ra | X | R | mp | $n_D^{25}$ |
|---|---|---|---|---|---|---|
| 85 | $CF_3$ | H | $\underset{OCN(Pr)_2}{\overset{O}{\parallel}}$ | Me | 62–64 | |
| 86 | $CF_3$ | H | $\underset{OC(pyrrolidinyl)}{\overset{O}{\parallel}}$ | Me | 73–75 | |
| 87 | $CF_3$ | H | $\underset{OCN(Me)_2}{\overset{O}{\parallel}}$ | Me | 58–59 | |
| 88 | $CF_3$ | H | $O^{\ominus}\overset{\oplus}{N}H_2(iPr)_2$ | Me | 94–104 | |
| 89 | $CF_3$ | H | $\underset{NHCCF_3}{\overset{O}{\parallel}}$ | Et | 83–86 | |
| 90 | $CF_3$ | H | $\underset{NHCCF_2CF_3}{\overset{O}{\parallel}}$ | Et | 43–46 | |
| 91 | $CF_3$ | H | $\underset{OP(OEt)_2}{\overset{S}{\parallel}}$ | Me | | 1.4454 |
| 92 | $CF_3$ | H | $\underset{OP(OMe)_2}{\overset{S}{\parallel}}$ | Me | 68–69 | |
| 93 | $CF_3$ | H | $\underset{OCPh}{\overset{O}{\parallel}}$ | Me | 121–122 | |
| 94 | $CF_3$ | H | $\underset{OCMe}{\overset{O}{\parallel}}$ | Me | 63–64 | |
| 95 | $CF_3$ | H | $\underset{OCCyHx}{\overset{O}{\parallel}}$ | Me | | 1.4425 |
| 96 | $CF_3$ | H | $\underset{OCtBu}{\overset{O}{\parallel}}$ | Me | | 1.4206 |
| 97 | $CF_3$ | H | $\underset{OC(Pr)}{\overset{O}{\parallel}}$ | Me | | 1.4214 |
| 98 | $CF_3$ | H | $\underset{OCiPr}{\overset{O}{\parallel}}$ | Me | | 1.4195 |
| 99 | $CF_3$ | H | $\underset{OCCyPr}{\overset{O}{\parallel}}$ | Me | 71–72 | |
| 100 | $CF_3$ | H | $O^{\ominus}\overset{\oplus}{N}H_3iPr$ | Me | 152–154 | |
| 101 | $CF_3$ | H | $O^{\ominus}\overset{\oplus}{N}H_3CyHx$ | Me | 135–137 | |
| 102 | $CF_3$ | H | $O^{\ominus}\overset{\oplus}{N}H_3tBu$ | Me | 141–143 | |
| 103 | $CF_3$ | H | $O^{\ominus}\overset{\oplus}{N}H_2(CyHx)_2$ | Me | 183–185 | |

PRE-EMERGENT HERBICIDE EXAMPLES

As noted above, many of the compounds of this invention has been found to be effective as pre-emergent and post-emergent herbicides. The preferred herbicidal compounds of this invention are compounds wherein R is lower alkyl, $R_2$ is selected from fluorinated methyl and chlorifluorinated methyl, and X is selected from $OR_3$ in which $R_3$ is hydrogen, arylsulfonyl, lower alkylcarbonyl, lower haloalkylcarbonyl, arylcarbonyl, aralkylcarbonyl, aryloxyacetyl, carboalkoxymethyl, and a cation. Table 3 summarizes results of tests conducted to determine the pre-emergent herbicidal activity of the compounds of this invention on common weeds.

The pre-emergent tests are conducted as follows:

Top soil is placed in aluminum pans and compacted to a depth of 0.95 to 1.27 cm. from the top of the pan. On the top of the soil is placed a predetermined number of seeds or vegetative propagules of various plant species. The soil required to level fill the pans after seedling or adding vegetative propagules is weighed into a pan. A known amount of the active ingredient applied in acetone as a solvent is thoroughly mixed with the soil, and the herbicide/soil mixture is used as a cover layer for prepared pans. In Table 3 below the amount of active ingredient is equal to the rate of 11.2 kg/ha. After treatment, the pans are moved to a greenhouse bench where they are watered from below as needed to give adequate moisture for germination and growth.

Approximately 10–14 days (usually 11 days) after seeding and treating, the pans are observed and the results recorded. In some instances, a second observation is made approximately 24–28 days after seeding and treating, and these observations are indicated in the following tables by an asterisk (*) immediately following the Example number.

Table 3 below summarizes the results of the pre-emergent herbicidal activity tests of compounds of this invention in weeds.

The herbicidal rating is obtained by means of a fixed scale based on the percent inhibition of each plant species. The symbols in the Table are defined as follows:

| % Inhibition | Rating |
|---|---|
| 0–24 | 0 |
| 25–49 | 1 |
| 50–74 | 2 |
| 75–100 | 3 |
| Not planted | — |
| Species planted, no data | N |

WEED-PLANT HERBICIDE ACTIVITY

The plant species usually regarded as weeds which are utilized in one set of tests, the data for which are shown in Table 3, are identified by letter headings above the columns in accordance with the following legend:

A - Canada thistle*
B - Cocklebur
C - Velvetleaf
D - Morningglory
E - Common Lambsquarters
F - Pennsylvania Smartweed
G - Yellow Nutsedge*
H - Quackgrass*
I - Johnsongrass*
J - Downy Brome
K - Barnyardgrass

*Grown from vegetative propagules

TABLE 3
PRE-EMERGENT ACTIVITY FOR WEEDS

| Example No. | Kg/ha | A | B | C | D | E | F | G | H | I | J | K |
|---|---|---|---|---|---|---|---|---|---|---|---|---|
| 3 | 11.2 | N | 0 | 3 | 2 | 3 | 3 | 0 | 0 | 0 | 0 | 0 |
| 4 | 11.2 | N | 0 | 0 | 0 | 3 | 0 | 0 | 0 | 0 | 0 | 0 |
| 5 | 11.2 | 0 | 0 | 0 | 0 | 1 | 0 | 0 | 0 | 0 | 0 | 3 |
| 6 | 11.2 | 0 | 0 | 0 | 0 | 0 | 0 | 0 | 0 | 0 | 0 | 0 |
| 7 | 11.2 | 0 | 0 | 0 | 2 | 1 | N | 0 | 3 | 0 | 1 | 3 |
| 8 | 11.2 | 0 | 0 | 0 | 0 | 0 | N | 0 | 0 | 0 | 1 | 0 |
| 9 | 11.2 | 0 | 0 | 0 | 0 | 1 | 0 | 0 | 0 | 0 | 0 | 0 |
| 10 | 11.2 | 0 | 0 | 0 | 0 | 1 | 1 | 0 | 0 | 0 | 2 | 3 |
| 11 | 11.2 | 0 | 0 | 0 | 0 | 0 | — | 0 | 0 | 0 | 0 | N |
| 12 | 11.2 | 0 | 0 | 0 | 0 | 1 | 1 | 0 | 0 | 0 | 0 | 3 |
| 13 | 11.2 | 0 | 0 | 0 | 1 | 1 | 2 | 0 | 0 | 0 | 3 | 3 |
| 14 | 11.2 | 0 | 3 | 0 | 3 | 1 | 3 | 0 | 1 | 0 | 3 | 3 |
| 15 | 11.2 | 0 | 0 | 0 | 0 | 0 | 0 | 0 | 0 | 0 | 0 | 0 |
| 16 | 11.2 | 0 | 0 | 0 | 0 | 0 | 0 | 0 | 0 | 0 | 0 | 0 |
| 17 | 11.2 | 0 | 0 | 0 | 0 | 0 | — | 0 | 3 | 0 | 0 | 0 |
| 18 | 11.2 | 0 | 0 | 0 | 0 | 2 | 0 | 0 | 0 | 0 | 0 | 0 |
| 19 | 11.2 | 0 | 0 | 0 | 0 | 0 | N | 0 | 0 | 0 | 0 | 0 |
| 20 | 11.2 | N | 0 | 0 | 0 | 0 | 0 | 0 | N | 0 | 0 | 0 |
| 21 | 11.2 | 0 | 0 | 0 | 0 | 3 | 0 | 0 | 0 | 0 | 0 | 0 |
| 22 | 11.2 | 0 | 0 | 0 | 0 | 0 | 0 | 0 | 0 | N | 0 | 0 |
| 23 | 11.2 | — | 0 | 0 | 0 | 0 | 0 | 0 | 0 | 0 | 0 | 0 |
| 24 | 11.2 | — | 0 | 0 | 0 | 0 | 0 | 0 | 0 | 0 | 0 | 0 |
| 25 | 11.2 | 0 | 0 | 0 | 0 | 1 | 0 | 0 | 0 | 0 | 0 | 1 |
| 26 | 11.2 | 0 | 0 | 0 | 0 | 3 | — | 0 | 2 | 0 | 0 | — |
| 27 | 11.2 | 0 | 0 | 0 | 0 | 0 | N | 0 | 0 | 0 | 0 | 1 |
| 28 | 11.2 | 0 | 0 | 0 | 0 | 2 | — | 0 | 0 | 0 | 0 | 3 |
| 29 | 11.2 | 0 | 0 | 0 | 3 | 3 | 3 | 0 | 0 | 0 | 3 | 3 |
| 30 | 11.2 | 0 | 0 | 0 | 0 | 0 | 0 | 0 | N | 0 | 0 | 1 |
| 31 | 11.2 | 0 | 0 | 0 | 0 | 3 | 0 | 0 | 0 | 0 | 3 | 1 |
| 32 | 11.2 | 0 | 2 | 0 | 0 | 0 | 0 | 0 | 0 | 0 | 0 | 0 |
| 33 | 11.2 | 0 | 0 | 0 | 0 | 0 | 0 | 0 | 0 | 0 | 0 | 0 |
| 35 | 22.4 | 3 | 3 | 3 | 3 | 3 | 3 | 0 | N | 3 | 0 | 0 |
| 35 | 16.8 | 0 | 0 | 3 | 3 | 3 | 0 | 0 | N | 0 | 0 | 0 |
| 35 | 11.2 | 0 | 1 | 3 | 3 | 3 | 0 | 0 | N | 0 | 0 | 0 |
| 35 | 11.2 | N | 3 | 3 | 3 | 3 | 3 | 0 | 0 | 0 | 0 | 0 |
| 35* | 11.2 | N | 2 | 3 | 2 | 3 | 3 | 0 | 0 | 0 | 0 | 0 |
| 35 | 11.2 | N | 0 | 1 | 3 | 3 | 0 | 0 | 0 | 0 | 0 | 0 |
| 35 | 11.2 | N | 0 | 3 | 3 | 3 | 0 | 0 | 0 | 0 | 0 | 0 |
| 35 | 5.6 | N | 0 | 0 | 3 | 3 | 0 | 0 | 0 | 0 | 0 | 0 |
| 35 | 5.6 | N | 0 | 1 | 3 | 2 | 0 | 0 | 0 | 0 | 0 | 0 |
| 35 | 5.6 | N | 0 | 1 | 3 | 3 | 0 | 0 | 0 | 0 | 0 | 0 |
| 36 | 11.2 | N | 0 | 1 | 1 | 2 | 0 | 0 | 0 | 0 | 3 | 0 |
| 37 | 11.2 | N | 0 | 0 | 0 | 0 | 0 | 0 | 0 | 0 | 0 | 0 |
| 38 | 11.2 | 0 | 0 | 0 | 3 | 1 | 0 | 0 | 0 | 0 | 0 | 2 |
| 39 | 11.2 | 0 | 0 | 0 | 0 | 0 | N | 0 | 0 | 0 | 0 | 3 |
| 40 | 11.2 | 0 | 1 | 3 | 3 | 3 | 0 | 0 | 0 | 0 | 0 | 0 |
| 41 | 11.2 | 0 | 0 | 2 | 3 | 3 | 3 | 0 | 0 | 0 | 0 | 0 |
| 42 | 11.2 | 0 | 0 | 0 | 1 | 3 | 0 | 0 | 0 | 0 | 0 | 0 |
| 42* | 11.2 | 3 | 0 | 0 | 1 | 3 | 0 | 0 | 0 | 0 | 0 | 0 |
| 43 | 11.2 | 2 | 2 | 3 | 3 | 3 | 3 | 0 | 0 | 0 | 1 | 0 |
| 43* | 11.2 | 2 | 2 | 3 | 3 | 3 | 3 | 0 | 0 | 0 | 0 | 0 |
| 44 | 11.2 | 2 | 0 | 3 | 1 | 3 | 2 | 0 | 0 | 0 | 0 | 0 |
| 44* | 11.2 | 3 | 0 | 3 | 1 | 3 | 3 | 0 | 0 | 0 | 0 | 0 |
| 45 | 11.2 | 3 | 0 | 0 | 1 | 3 | 0 | 0 | 0 | 0 | 0 | 0 |
| 46 | 11.2 | 1 | 0 | 1 | 1 | 3 | 1 | 0 | 0 | 0 | 0 | 0 |
| 46* | 11.2 | 3 | 0 | 2 | 1 | 3 | 1 | 0 | 0 | 0 | 0 | 0 |
| 47 | 11.2 | 0 | 0 | 0 | 0 | 0 | 0 | 0 | 0 | 0 | 0 | 0 |
| 48 | 11.2 | 0 | 0 | 0 | 0 | 0 | 0 | 0 | 0 | 0 | 0 | 0 |
| 49 | 11.2 | 0 | 0 | 0 | 0 | 3 | 0 | 0 | 0 | 0 | 0 | 0 |
| 50 | 11.2 | 0 | 0 | 3 | 1 | 3 | 3 | 0 | 0 | 0 | 0 | 0 |
| 51 | 11.2 | 2 | 0 | 3 | 2 | 3 | 0 | 0 | 0 | 0 | 0 | 0 |
| 51* | 11.2 | 0 | 0 | 3 | 2 | 3 | 0 | 0 | 0 | 0 | 0 | 0 |
| 52 | 11.2 | 1 | 0 | 3 | 3 | 3 | 2 | 0 | 0 | 0 | 0 | 0 |
| 53 | 11.2 | 1 | 0 | 1 | 2 | 3 | 1 | 0 | 0 | 0 | 0 | 0 |
| 54 | 11.2 | 3 | 2 | 3 | 3 | 2 | 1 | 0 | 3 | 0 | 1 | 1 |
| 54* | 11.2 | 3 | 2 | 3 | 3 | 1 | 0 | 2 | 0 | 1 | 0 | 0 |
| 55 | 11.2 | — | 0 | 0 | 0 | 3 | N | 0 | 0 | 0 | 0 | 0 |
| 56 | 11.2 | — | 0 | 1 | 3 | 3 | 3 | 0 | 0 | 0 | 0 | 2 |
| 57 | 11.2 | — | 0 | 0 | 1 | 3 | 3 | 0 | 0 | 0 | 0 | 2 |
| 58 | 11.2 | 0 | 0 | 0 | 1 | 3 | 0 | 0 | 0 | 0 | 0 | 0 |
| 59 | 11.2 | 0 | 0 | 2 | 1 | 3 | 1 | 0 | 0 | 0 | 0 | 0 |
| 60 | 11.2 | 0 | 0 | 2 | 1 | 3 | 1 | 0 | 0 | 0 | 0 | 0 |
| 60* | 11.2 | 0 | 0 | 3 | 1 | 3 | 1 | 0 | 0 | 0 | 0 | 0 |
| 61 | 11.2 | 3 | 0 | 2 | 3 | 3 | 1 | 0 | 0 | 0 | 0 | 0 |
| 61* | 11.2 | 3 | 0 | 2 | 3 | 3 | 0 | 0 | 0 | 0 | 0 | 0 |
| 62 | 11.2 | 3 | 3 | 3 | 3 | 3 | — | 1 | 1 | 1 | 3 | 3 |
| 62* | 11.2 | 3 | 3 | 3 | 3 | 3 | — | 0 | 0 | 0 | 2 | 2 |
| 63 | 11.2 | 2 | 0 | 0 | 1 | 3 | 1 | 0 | 0 | 0 | 0 | 0 |
| 64 | 11.2 | 0 | 0 | 0 | 0 | 3 | 0 | 0 | 0 | 0 | 0 | 0 |
| 65 | 11.2 | 0 | 0 | 0 | 0 | 0 | 0 | 0 | 0 | 0 | 0 | 0 |
| 66 | 11.2 | 0 | 0 | 0 | 0 | 0 | — | 0 | 0 | 0 | 0 | — |
| 67 | 11.2 | 3 | 0 | 0 | 0 | 0 | — | 0 | 0 | 0 | 0 | 0 |
| 67* | 11.2 | 0 | 0 | 0 | 0 | 0 | 0 | 0 | 0 | 0 | 0 | 0 |
| 68 | 11.2 | 0 | 0 | 0 | 0 | 3 | — | 0 | 0 | 0 | 0 | 0 |
| 69 | 11.2 | N | 0 | 0 | 0 | 3 | 0 | 0 | 0 | 0 | 0 | 0 |
| 70 | 11.2 | N | 0 | 0 | 3 | 3 | 1 | 0 | 3 | 1 | 0 | 0 |
| 71 | 11.2 | 0 | 0 | 0 | 2 | 1 | 1 | 0 | 0 | 0 | 0 | 1 |
| 72 | 11.2 | 0 | 0 | 0 | 0 | 3 | 0 | 0 | 0 | 0 | 0 | 0 |
| 73 | 11.2 | 0 | 0 | 1 | 0 | 2 | 0 | 0 | 0 | 0 | 0 | 0 |
| 74 | 11.2 | 0 | 0 | 0 | 0 | 0 | 0 | 0 | 0 | 0 | 0 | 0 |
| 75 | 11.2 | 0 | 0 | 3 | 2 | 2 | 0 | 0 | 0 | 0 | 0 | 0 |
| 76 | 11.2 | 0 | 0 | 0 | 1 | 1 | 0 | 0 | 0 | 0 | 0 | 0 |
| 77 | 11.2 | 2 | 1 | 3 | 3 | 3 | 3 | 0 | 0 | 0 | 3 | 0 |
| 77* | 11.2 | 3 | 1 | 3 | 3 | 3 | 3 | 0 | 0 | 0 | 3 | 0 |
| 78 | 11.2 | 1 | 3 | 3 | 3 | 3 | 3 | 0 | 2 | 0 | 1 | 0 |
| 78* | 11.2 | 2 | 3 | 3 | 3 | 3 | 3 | 0 | 2 | 0 | 2 | 0 |
| 79 | 11.2 | 1 | 2 | 3 | 3 | 3 | 3 | 0 | 0 | 0 | 0 | 0 |
| 79* | 11.2 | 0 | 3 | 3 | 3 | 3 | 3 | 0 | 0 | 0 | 0 | 0 |
| 80 | 11.2 | 0 | 0 | 0 | 0 | 0 | 1 | 0 | 0 | 0 | 0 | 0 |
| 81[1] | 11.2 | 0 | 0 | 0 | 1 | 3 | 2 | 0 | 0 | 3 | 0 | 1 |
| 81* | 11.2 | 0 | 0 | 0 | 0 | 3 | 0 | 0 | 0 | 0 | 0 | 0 |
| 82 | 11.2 | 0 | 0 | 0 | 0 | 3 | 0 | 0 | 0 | 0 | 0 | 0 |
| 83 | 11.2 | 0 | 0 | 0 | 1 | 3 | 2 | 0 | 1 | 0 | 0 | 2 |
| 84[1] | 11.2 | 0 | 0 | 0 | 1 | 3 | 3 | 0 | 0 | 3 | 0 | 3 |
| 84* | 11.2 | 0 | 0 | 0 | 0 | N | 0 | 0 | 0 | 0 | 0 | 0 |
| 85[1] | 11.2 | 0 | 0 | 0 | 1 | 3 | 3 | 0 | 0 | 0 | 0 | 0 |
| 85* | 11.2 | 0 | 0 | 0 | 0 | 0 | 0 | 0 | 0 | 0 | 0 | 0 |
| 86 | 11.2 | 1 | 0 | 0 | 0 | 3 | 3 | 0 | 0 | 0 | 0 | 3 |
| 87 | 11.2 | 0 | 0 | 0 | 0 | 3 | 0 | 1 | 1 | 0 | 0 | 1 |
| 88 | 11.2 | 0 | 0 | 1 | 2 | 3 | 1 | 0 | 0 | 0 | 0 | 3 |
| 89 | 11.2 | N | N | 0 | 0 | 0 | 0 | 0 | 0 | 0 | 0 | 0 |
| 90 | 11.2 | N | 0 | 0 | 0 | 3 | 0 | 0 | 0 | 0 | 0 | 0 |
| 91 | 11.2 | — | 0 | 1 | 0 | 3 | 1 | 0 | 2 | 0 | 0 | 1 |
| 92 | 11.2 | — | 0 | 0 | 3 | 3 | 1 | 0 | 3 | 0 | 0 | 0 |
| 92* | 11.2 | 0 | 0 | 1 | 0 | 3 | 0 | 0 | 0 | 0 | 0 | 0 |
| 93 | 11.2 | 1 | 1 | 0 | 0 | 3 | 2 | 0 | 0 | 0 | 0 | 0 |
| 94 | 11.2 | 1 | 0 | 0 | 0 | 3 | 1 | 0 | 0 | 0 | 0 | 0 |
| 95 | 11.2 | 0 | 0 | 0 | 0 | 3 | 2 | 0 | 0 | 0 | 0 | 3 |
| 96 | 11.2 | 0 | 0 | 1 | 0 | 3 | 2 | 0 | 0 | 0 | 0 | 0 |
| 97 | 11.2 | 1 | 0 | 1 | 0 | 3 | 2 | 0 | 0 | 3 | 0 | 0 |
| 97* | 11.2 | 0 | 0 | 0 | 0 | 3 | 0 | 0 | 0 | 3 | 0 | 0 |
| 97* | 11.2 | 0 | 0 | 0 | 0 | 3 | 2 | 0 | 1 | 0 | 0 | 1 |
| 98 | 11.2 | 0 | 0 | 0 | 0 | 3 | 1 | 0 | 0 | 0 | 0 | 0 |
| 99 | 11.2 | 0 | 0 | 0 | 1 | 3 | 2 | 0 | 0 | 3 | 0 | 0 |
| 99* | 11.2 | 0 | 0 | 0 | 0 | 3 | 0 | 0 | 0 | 0 | 0 | 0 |
| 100 | 11.2 | 0 | 0 | 0 | 0 | 3 | 1 | 0 | 0 | 0 | 0 | 0 |
| 101 | 11.2 | 0 | 0 | 0 | 0 | 3 | 1 | 0 | 0 | 3 | 0 | 0 |
| 101* | 11.2 | 1 | 0 | 1 | 0 | 3 | 1 | 0 | 0 | 0 | 0 | 0 |
| 102 | 11.2 | 0 | 0 | 0 | 0 | 2 | 0 | 0 | 0 | 0 | 0 | 0 |
| 103 | 11.2 | 0 | 0 | 0 | 1 | 2 | 1 | 0 | 0 | 0 | 0 | 0 |

[1]Possibly contaminated sample

CROP AND WEED PLANT HERBICIDE ACTIVITY

The compounds were further tested by utilizing the above procedure on the following plant species, i.e., on weeds in the presence of crop plants.

L - Soybean
M - Sugarbeet
N - Wheat
O - Rice
P - Grain Sorghum
B - Cocklebur
Q - Wild Buckwheat
D - Morningglory
R - Hemp Sesbania
E - Common Lambsquarters
F - Pennsylvania Smartweed
C - Velvetleaf
J - Downy Brome
S - Panicum spp.
K - Barnyardgrass
T - Large Crabgrass The results are summarized in Table 4.

TABLE 4

PRE-EMERGENT ACTIVITY FOR WEEDS IN CROP PLANTS

| Example No. | kg/ha | L | M | N | O | P | B | Q | D | R | E | F | C | J | S | K | T |
|---|---|---|---|---|---|---|---|---|---|---|---|---|---|---|---|---|---|
| 3 | 5.6 | 0 | 1 | 0 | 0 | 0 | 0 | 0 | 0 | 0 | 2 | 0 | 0 | 0 | 0 | 0 | 0 |
|  | 1.12 | 0 | 0 | 0 | 0 | 0 | 0 | 0 | 0 | 0 | 0 | N | 0 | 0 | 0 | 0 | 0 |
|  | 0.28 | 0 | 0 | 0 | 0 | 0 | 0 | 0 | 0 | 0 | 0 | 0 | 0 | 0 | 0 | 0 | 0 |
| 5 | 5.6 | 0 | 3 | 0 | 0 | 0 | 0 | 3 | 1 | 1 | 3 | 2 | 1 | 0 | 0 | 0 | 0 |
|  | 1.12 | 0 | 0 | 0 | 0 | 0 | 0 | 0 | 0 | 0 | 0 | 0 | 0 | 0 | 0 | 0 | 0 |
| 7 | 5.6 | 0 | 2 | 1 | 0 | 0 | 0 | 0 | 0 | 0 | 1 | 1 | 0 | 2 | 2 | 3 | 3 |
|  | 1.12 | 0 | 1 | 0 | 0 | 0 | 0 | 0 | 0 | 0 | 1 | 0 | 0 | 1 | 0 | 0 | 2 |
|  | 0.28 | 0 | 0 | 0 | 0 | 0 | 0 | 0 | 0 | 0 | 0 | 0 | 0 | 0 | 0 | 0 | 0 |
| 10 | 5.6 | 0 | 0 | 0 | 0 | 0 | 0 | 0 | 0 | 0 | 0 | — | 0 | 0 | 0 | 0 | 0 |
|  | 1.12 | 0 | 0 | 0 | 0 | 0 | 0 | 0 | 0 | 0 | 0 | — | 0 | 0 | 0 | 0 | 0 |
| 12 | 5.6 | N | 0 | 0 | 0 | 0 | 0 | 0 | 0 | 0 | 1 | 1 | 0 | 0 | 1 | 2 | 1 |
|  | 1.12 | 0 | 0 | 0 | 0 | 0 | 0 | 0 | 0 | 0 | 0 | 0 | 0 | 0 | 0 | 0 | 0 |
| 13 | 5.6 | 0 | 2 | 0 | 0 | 0 | 0 | 0 | 0 | 0 | 1 | 1 | 0 | 1 | 0 | 1 | 3 |
|  | 1.12 | 0 | 0 | 0 | 0 | 0 | 0 | 0 | 0 | 0 | 0 | 0 | 0 | 0 | 0 | 0 | 0 |
| 14 | 5.6 | 1 | 2 | 1 | 3 | 3 | 0 | 2 | 1 | 1 | 2 | 2 | 0 | 3 | 3 | 2 | 3 |
|  | 1.12 | 0 | 0 | 0 | 0 | 0 | 0 | 0 | 0 | 0 | 0 | 0 | 0 | 0 | 0 | 0 | 0 |
|  | 0.28 | 0 | 0 | 0 | 0 | 0 | 0 | 0 | 0 | 0 | 0 | 0 | 0 | 0 | 0 | 0 | 0 |
| 28 | 5.6 | 0 | 0 | 0 | 0 | 0 | 0 | 0 | 0 | 0 | 0 | — | 0 | 0 | 0 | 0 | 0 |
|  | 1.12 | 0 | 0 | 0 | 0 | 0 | 0 | 0 | 0 | 0 | 1 | — | 0 | 0 | 0 | 0 | 0 |
| 29 | 5.6 | 0 | 3 | 2 | 0 | 3 | 0 | 2 | 2 | 2 | 2 | 2 | 1 | 1 | 2 | 3 | 3 |
|  | 1.12 | 0 | 0 | 0 | 0 | 0 | 0 | 0 | 0 | 0 | 1 | 1 | 0 | 0 | 1 | 0 | 2 |
|  | 0.28 | 0 | 0 | 0 | 0 | 0 | 0 | 0 | 0 | 0 | 0 | 0 | 0 | 0 | 0 | 0 | 1 |
| 31 | 5.6 | 2 | 3 | 0 | 0 | 2 | 2 | 2 | 3 | 2 | 3 | 3 | 1 | 2 | 2 | 2 | 3 |
|  | 1.12 | 0 | 0 | 0 | 0 | 0 | 0 | 0 | 0 | 0 | 0 | 0 | 0 | 0 | 0 | 0 | 0 |
| 35 | 11.12 | 0 | 1 | 0 | 0 | 0 | 0 | 0 | 0 | 0 | 0 | 0 | 0 | 0 | 0 | 0 | 0 |
|  | 5.6 | 0 | 2 | 3 | 1 | 0 | 0 | 0 | 2 | 1 | 2 | 1 | 0 | 0 | 1 | 1 | 0 |
|  | 5.6 | 0 | 0 | 0 | 0 | 0 | 0 | 0 | 0 | 0 | 0 | 0 | 0 | 0 | 0 | 0 | 0 |
|  | 5.6 | 0 | 1 | 0 | 0 | 0 | 0 | 0 | 0 | 0 | 0 | 0 | 0 | 0 | 0 | 0 | 0 |
|  | 5.6 | 0 | 2 | 0 | 0 | 0 | 0 | 0 | 0 | 0 | 0 | 0 | 0 | 0 | 0 | 0 | 0 |
|  | 0.28 | 0 | 0 | 0 | 0 | 0 | 0 | 0 | 0 | 0 | 0 | 0 | 0 | 0 | 0 | 0 | 0 |
|  | 0.056 | 0 | 0 | 0 | 0 | 0 | 0 | 0 | 0 | 0 | 0 | 0 | 0 | 0 | 0 | 0 | 0 |
| 36 | 5.6 | 0 | 1 | 0 | 0 | 0 | 0 | 0 | 0 | 0 | 0 | 0 | 0 | 0 | 0 | 0 | 1 |
|  | 1.12 | 0 | 0 | 0 | 0 | 0 | 0 | 0 | 0 | 0 | 0 | 0 | 0 | 0 | 0 | 0 | 0 |
| 38 | 5.6 | 0 | 2 | 0 | 0 | 0 | 0 | 0 | 1 | 0 | 1 | 1 | 2 | 0 | 0 | 2 | 2 |
|  | 1.12 | 0 | 0 | 0 | 0 | 0 | 0 | 0 | 0 | 0 | 0 | 0 | 0 | 0 | 0 | 0 | 0 |
|  | 0.28 | 0 | 0 | 0 | 0 | 0 | 0 | 0 | 0 | 0 | 0 | 0 | 0 | 0 | 0 | 0 | 0 |
| 40 | 5.6 | 0 | 3 | 0 | 1 | 0 | 0 | 2 | 2 | 3 | 3 | 1 | 0 | 0 | 0 | 0 | 0 |
|  | 1.12 | 0 | 0 | 0 | 0 | 0 | 0 | 0 | 0 | 0 | 0 | 0 | 0 | 0 | 0 | 0 | 0 |
|  | 0.28 | 0 | 0 | 0 | 0 | 0 | 0 | 0 | 0 | 0 | 0 | 0 | 0 | 0 | 0 | 0 | 0 |
|  | 0.058 | 0 | 0 | 0 | 0 | 0 | 0 | 0 | 0 | 0 | 0 | 0 | 0 | 0 | 0 | 0 | 0 |
| 41 | 5.6 | 0 | 3 | 0 | 0 | 0 | 0 | 0 | 0 | 0 | 0 | 0 | 0 | 0 | 0 | 0 | 0 |
|  | 1.12 | 0 | 3 | 0 | 0 | 0 | 0 | 0 | 0 | 0 | 0 | 0 | 0 | 0 | 0 | 0 | 0 |
|  | 0.28 | 0 | 0 | 0 | 0 | 0 | 0 | 0 | 0 | 0 | 0 | 0 | 0 | 0 | 0 | 0 | 0 |
|  | 0.058 | 0 | 0 | 0 | 0 | 0 | 0 | 0 | 0 | 0 | 0 | 0 | 0 | 0 | 0 | 0 | 0 |
| 43 | 5.6 | 0 | 3 | 0 | 0 | 0 | 1 | 3 | 3 | 3 | 3 | 3 | 2 | 0 | 0 | 0 | 0 |
|  | 1.12 | 0 | 3 | 0 | 0 | 0 | 0 | 0 | 0 | 3 | 1 | 0 | 0 | 0 | 0 | 0 | 0 |
|  | 0.28 | 0 | 2 | 0 | 0 | 0 | 0 | 0 | 0 | 0 | 0 | 0 | 0 | 0 | 0 | 0 | 0 |
|  | 0.058 | 0 | 0 | 0 | 0 | 0 | 0 | 0 | 0 | 0 | 0 | 0 | 0 | 0 | 0 | 0 | 0 |
| 44 | 5.6 | 0 | 3 | 0 | 0 | 0 | 0 | 3 | 2 | 0 | 3 | 3 | 1 | 0 | 0 | 0 | 0 |
|  | 1.12 | 0 | 1 | 0 | 1 | 0 | 0 | 0 | 0 | 0 | 1 | 0 | 0 | 0 | 0 | 0 | 0 |
|  | 0.28 | 0 | 0 | 0 | 0 | 0 | 0 | 0 | 0 | 0 | 0 | 0 | 0 | 0 | 0 | 0 | 0 |
| 50 | 5.6 | 0 | 3 | 0 | 0 | 0 | 0 | 3 | 1 | 3 | 3 | 1 | 0 | 0 | 0 | 0 | 0 |
|  | 1.12 | 0 | 0 | 0 | 0 | 0 | 0 | 1 | 0 | 0 | 0 | 0 | 0 | 0 | 0 | 0 | 0 |
|  | 0.28 | 0 | 0 | 0 | 0 | 0 | 0 | 0 | 0 | 0 | 0 | 0 | 0 | 0 | 0 | 0 | 0 |
| 51 | 5.6 | 0 | 0 | 0 | 0 | 0 | 0 | 0 | 0 | 0 | 1 | 0 | 1 | 0 | 0 | 0 | 0 |
|  | 1.12 | 0 | 0 | 0 | 0 | 0 | 0 | 0 | 0 | 0 | 0 | 0 | 0 | 0 | 0 | 0 | 0 |
|  | 0.28 | 0 | 0 | 0 | -0 | 0 | 0 | 0 | 0 | 0 | 0 | 0 | 0 | 0 | 0 | 0 | 0 |
| 52 | 5.6 | 0 | 3 | 0 | 0 | 0 | 3 | 3 | 1 | 3 | 3 | N | 2 | 0 | 0 | 0 | 0 |
|  | 1.12 | 0 | 3 | 0 | 0 | 0 | 0 | 0 | 0 | 0 | 1 | N | 1 | 0 | 0 | 0 | 0 |
|  | 0.28 | 0 | 0 | 0 | 0 | 0 | 0 | 0 | 0 | 0 | 0 | N | 0 | 0 | 0 | 0 | 0 |
| 54 | 5.6 | 2 | 3 | 0 | 1 | 0 | 0 | 0 | 1 | 1 | 3 | — | 2 | 1 | 1 | 1 | 1 |
|  | 1.12 | 0 | 0 | 0 | 0 | 0 | 0 | 0 | 0 | 0 | 2 | — | 0 | 0 | 0 | 0 | 0 |
|  | 0.28 | 0 | 0 | 0 | 0 | 0 | 0 | 0 | 0 | 0 | 3 | — | 0 | 0 | 0 | 0 | 0 |
|  | 0.058 | 0 | 0 | 0 | 0 | 0 | 0 | 0 | 0 | 0 | 0 | — | 0 | 0 | 0 | 0 | 0 |
| 56 | 5.6 | 0 | 3 | 0 | 0 | 0 | 3 | 0 | 0 | 0 | 2 | 2 | 1 | 0 | 0 | 1 | 2 |
|  | 1.12 | 0 | 0 | 0 | 0 | 0 | 0 | 0 | 0 | 0 | 0 | 0 | 0 | 0 | 0 | 0 | 0 |
|  | 0.28 | 0 | 0 | 0 | 0 | 0 | 0 | 0 | 0 | 0 | 0 | 0 | 0 | 0 | 0 | 0 | 0 |
| 57 | 5.6 | 0 | 3 | 0 | 0 | 0 | 0 | 2 | 1 | 0 | 2 | 2 | 0 | 0 | 0 | 0 | 0 |
|  | 1.12 | 0 | 0 | 0 | 0 | 0 | 0 | 0 | 0 | 0 | 0 | 0 | 0 | 0 | 0 | 0 | 0 |
|  | 0.28 | 0 | 0 | 0 | 0 | 0 | 0 | 0 | 0 | 0 | 0 | 0 | 0 | 0 | 0 | 0 | 0 |
| 60 | 5.6 | 0 | 3 | 0 | 0 | 0 | 0 | 2 | 3 | 3 | 3 | — | 2 | 0 | 0 | 0 | 0 |
|  | 1.12 | 0 | 3 | 0 | 0 | 0 | 0 | 0 | 0 | 0 | 3 | — | 1 | 0 | 0 | 0 | 0 |
| 61 | 5.6 | 0 | 3 | 0 | 0 | 0 | 0 | 0 | 0 | 2 | 3 | — | 1 | 0 | 0 | 0 | 0 |

TABLE 4-continued

PRE-EMERGENT ACTIVITY FOR WEEDS IN CROP PLANTS

| Example No. | kg/ha | L | M | N | O | P | B | Q | D | R | E | F | C | J | S | K | T |
|---|---|---|---|---|---|---|---|---|---|---|---|---|---|---|---|---|---|
| | 1.12 | 0 | 3 | 0 | 0 | 0 | 0 | 0 | 0 | 0 | 2 | — | 0 | 0 | 0 | 0 | 0 |
| | 0.28 | 0 | 0 | 0 | 0 | 0 | 0 | 0 | 0 | 0 | 0 | — | 0 | 0 | 0 | 0 | 0 |
| 62 | 5.6 | 3 | 3 | 0 | 2 | 2 | 2 | 3 | 3 | 3 | 3 | — | 2 | 1 | 2 | 2 | 2 |
| | 1.12 | 2 | 2 | 0 | 1 | 1 | 0 | 2 | 2 | 1 | 2 | — | 1 | 1 | 0 | 1 | 2 |
| | 0.28 | 1 | 1 | 0 | 0 | 0 | 0 | 0 | 1 | 0 | 1 | — | 0 | 0 | 0 | 0 | 0 |
| | 0.058 | 0 | 0 | 0 | 0 | 0 | 0 | 0 | 0 | 0 | 0 | — | 0 | 0 | 0 | 0 | 0 |
| | 0.0112 | 0 | 0 | 0 | 0 | 0 | 0 | 0 | 0 | 0 | 0 | — | 0 | 0 | 0 | 0 | 0 |
| 70 | 5.6 | 0 | 1 | 0 | 0 | 0 | 0 | 0 | 1 | 0 | 2 | 2 | 0 | 0 | 0 | 0 | 0 |
| | 1.12 | 0 | 0 | 0 | 0 | 0 | 0 | 0 | 0 | 0 | 0 | 1 | 0 | 0 | 0 | 0 | 0 |
| | 0.28 | 0 | 0 | 0 | 0 | 0 | 0 | 0 | 0 | 0 | 0 | 0 | 0 | 0 | 0 | 0 | 0 |
| 75 | 5.6 | 0 | 2 | 0 | 0 | 0 | 0 | 0 | 0 | 0 | 0 | 0 | 0 | 0 | 0 | 0 | 0 |
| | 1.12 | 0 | 0 | 0 | 0 | 0 | 0 | 0 | 0 | 0 | 0 | 0 | 0 | 0 | 0 | 0 | 0 |
| | 0.28 | 0 | 0 | 0 | 0 | 0 | 0 | 0 | 0 | 0 | 0 | 0 | 0 | 0 | 0 | 0 | 0 |
| 77 | 5.6 | 0 | 1 | 0 | 1 | 0 | 0 | 1 | 0 | 0 | 3 | 1 | 0 | 2 | 1 | 0 | 1 |
| | 1.12 | 0 | 0 | 0 | 1 | 0 | 0 | 0 | 0 | 0 | 2 | 0 | 0 | 0 | 0 | 0 | 1 |
| | 0.28 | 0 | 0 | 0 | 0 | 0 | 0 | 0 | 0 | 0 | 1 | 0 | 0 | 0 | 0 | 0 | 1 |
| | 0.056 | 0 | 0 | 0 | 0 | 0 | 0 | 0 | 0 | 0 | 0 | 0 | 0 | 0 | 0 | 0 | 0 |
| 86 | 5.6 | 0 | 1 | 0 | 0 | 0 | 0 | 3 | 0 | 0 | 3 | 0 | 0 | 3 | 1 | 0 | 3 |
| | 1.12 | 0 | 0 | 0 | 0 | 0 | 0 | 3 | 0 | 0 | 3 | 0 | 0 | 0 | 0 | 0 | 1 |
| | 0.28 | 0 | 0 | 0 | 0 | 0 | 0 | 2 | 0 | 0 | 1 | 0 | 0 | 0 | 0 | 0 | 0 |
| 88 | 5.6 | 0 | 2 | 0 | 0 | 0 | 0 | 0 | 1 | 0 | 1 | 2 | 1 | 0 | 0 | 1 | 2 |
| | 1.12 | 0 | 0 | 0 | 0 | 0 | 0 | 0 | 0 | 0 | 0 | 1 | 0 | 0 | 0 | 0 | 0 |
| | 0.28 | 0 | 0 | 0 | 0 | 0 | 0 | 0 | 0 | 0 | 0 | 0 | 0 | 0 | 0 | 0 | 0 |
| 95 | 5.6 | 0 | 1 | 0 | 1 | 1 | 0 | 3 | 1 | 1 | 3 | 0 | 0 | 0 | 1 | 1 | 2 |
| | 1.12 | 0 | 0 | 0 | 0 | 1 | N | 3 | 0 | 1 | 1 | 0 | 0 | 0 | 1 | 1 | 1 |
| | 0.28 | 0 | 1 | 0 | 1 | 0 | 0 | 2 | 0 | 0 | 0 | 1 | 0 | 2 | 0 | 0 | 2 |

POST-EMERGENT HERBICIDE EXAMPLES

The post-emergence herbicidal activity of some of the various compounds of this invention was demonstrated by greenhouse testing in the following manner. Top soil is placed in aluminum pans having holes in the bottom and compacted to a depth of 0.95 to 1.27 cm. from the top of the pan. A predetermined number of seeds of each of several dicotyledonous and monocotyledonous annual plant species and/or vegetative propagules for the perennial plant species were placed on the soil and pressed into the soil surface. The seeds and/or vegetative propagules are covered with soil and leveled. The pans are then placed on a sand bench in the greenhouse and watered from below as needed. After the plants reach the desired age (two to three weeks), each pan, is removed individually to a spraying chamber and sprayed by means of an atomizer, operating at a spray pressure of 170.3 kPa (10 psig) at the application rates noted. In the spray solution is an amount of an emulsifying agent mixture to give a spray solution or suspension which contains about 0.4% by volume of the emulsifier. The spray solution or suspension contains a sufficient amount of the candidate chemical in order to give application rates of the active ingredient corresponding to those shown in the Tables while applying a total amount of solution or suspension equivalent to 1870 L/Ha (200 gallons/acre). The pans were returned to the greenhouse and watered as before and the injury to the plants as compared to the control is observed at approximately 10–14 days (usually 11 days) and in some instances observed again at 24–28 days (usually 25 days) after spraying. These latter observations are designated by an asterisk (*) following the column of example numbers in the Table.

The post-emergent herbicidal activity index used in Tables 4 and 5 is as follows:

| Plant Response | Index |
|---|---|
| 0–24% inhibition | 0 |
| 25–49% inhibition | 1 |
| 50–74% inhibition | 2 |
| 75–99% inhibition | 3 |
| 100% inhibition | 4 |
| Species not planted | — |
| Species planted, no data | N |

TABLE 5

POST-EMERGENT ACTIVITY FOR WEEDS

| Example No. | Kg/ha | A | B | C | D | E | F | G | H | I | J | K |
|---|---|---|---|---|---|---|---|---|---|---|---|---|
| 3 | 11.2 | N | 3 | 2 | 2 | 0 | 1 | 0 | 0 | 2 | 0 | 0 |
| 4 | 11.2 | 0 | 2 | 0 | 1 | 0 | 0 | 0 | 0 | 0 | 0 | 0 |
| 5 | 11.2 | 2 | 1 | 4 | 0 | 1 | — | 1 | 0 | 0 | 0 | 0 |
| 6 | 11.2 | 0 | 0 | 0 | 0 | 0 | 0 | 0 | 0 | 0 | 0 | 0 |
| 7 | 11.2 | N | 0 | 0 | 0 | 0 | 0 | 0 | 0 | 0 | 0 | 0 |
| 8 | 11.2 | 0 | 0 | 0 | 0 | 0 | 0 | 0 | N | 0 | 0 | 0 |
| 9 | 11.2 | 0 | 0 | 0 | 0 | 0 | 0 | 0 | 0 | 0 | 0 | 0 |
| 10 | 11.2 | 0 | 0 | 0 | 0 | 0 | 0 | 0 | 0 | 0 | 0 | 0 |
| 11 | 11.2 | 0 | 0 | 0 | 0 | 0 | — | 0 | 0 | 0 | 0 | 0 |
| 12 | 11.2 | 0 | 0 | 0 | 0 | 0 | N | 0 | 0 | 0 | 0 | 0 |
| 13 | 11.2 | 0 | 0 | 0 | 0 | 0 | 0 | 0 | 0 | 0 | 0 | 0 |
| 14 | 11.2 | 0 | 0 | 0 | 0 | 0 | 0 | 0 | 0 | 0 | 0 | 0 |
| 15 | 11.2 | 0 | 0 | 1 | 0 | 0 | 0 | 0 | 0 | 0 | 0 | 0 |
| 16 | 11.2 | 0 | 0 | 0 | 0 | 0 | 0 | 0 | 0 | 0 | 0 | 0 |
| 17 | 11.2 | 0 | 0 | 0 | 0 | 0 | — | 0 | 0 | 0 | 0 | 0 |
| 18 | 11.2 | 0 | 1 | 1 | 1 | 0 | 2 | 0 | 0 | 0 | 0 | 1 |
| 19 | 11.2 | 0 | 0 | 0 | 0 | 0 | 0 | 0 | 0 | 0 | 0 | 0 |
| 20 | 11.2 | N | 0 | 0 | 0 | 0 | 0 | 0 | 0 | 0 | 0 | 0 |
| 21 | 11.2 | 1 | 1 | 1 | 1 | 3 | 0 | 0 | 0 | 0 | 0 | 0 |
| 22 | 11.2 | 0 | 0 | 0 | 0 | 0 | 0 | 0 | 0 | 0 | 0 | 0 |
| 23 | 11.2 | — | 1 | 0 | 0 | 0 | 0 | 0 | 0 | 0 | 1 | 1 |
| 24 | 11.2 | — | 1 | 3 | 1 | 4 | 4 | 0 | 0 | 1 | 1 | 2 |
| 25 | 11.2 | 0 | 0 | 0 | 0 | 0 | 0 | 0 | 0 | 0 | 0 | 0 |
| 26 | 11.2 | 0 | 1 | 0 | 0 | 0 | — | 0 | 0 | 0 | 0 | 0 |
| 27 | 11.2 | 0 | 0 | 0 | 0 | 0 | 0 | 0 | 0 | 0 | 0 | 0 |
| 28 | 11.2 | 0 | 0 | 0 | 0 | 0 | 0 | 0 | 0 | 0 | 0 | 0 |
| 29 | 11.2 | 0 | 0 | 0 | 0 | 0 | 0 | 0 | 0 | 0 | 0 | 0 |
| 30 | 11.2 | 0 | 0 | 0 | 0 | 0 | 0 | N | 0 | 0 | 0 | 0 |
| 31 | 11.2 | 0 | 1 | 0 | 0 | 2 | 0 | 0 | 0 | 0 | 0 | 0 |
| 32 | 11.2 | N | 0 | 0 | 0 | 0 | 0 | 0 | 0 | 0 | 0 | 0 |
| 33 | 11.2 | 0 | N | 0 | 0 | 0 | 0 | 0 | 0 | 0 | 0 | 0 |
| 35 | 11.2 | N | 2 | 1 | 1 | 3 | 3 | 1 | 0 | 1 | 0 | 2 |
| 35* | 11.2 | N | 2 | 2 | 1 | 3 | 3 | 0 | 1 | 1 | 1 | 2 |
| 35 | 5.6 | N | 2 | 0 | 1 | 3 | 0 | 0 | 0 | 1 | 0 | 0 |
| 35* | 5.6 | N | 2 | 1 | 1 | 2 | 0 | 0 | 0 | 0 | 0 | 0 |

TABLE 5-continued
POST-EMERGENT ACTIVITY FOR WEEDS

| Example No. | Kg/ha | A | B | C | D | E | F | G | H | I | J | K |
|---|---|---|---|---|---|---|---|---|---|---|---|---|
| 36 | 11.2 | N | 0 | 0 | 0 | 0 | 0 | 0 | 0 | 0 | 0 | 0 |
| 37 | 11.2 | N | 0 | 0 | 0 | 0 | 0 | 0 | 0 | 0 | 0 | 0 |
| 38 | 11.2 | N | 0 | 0 | 0 | 0 | 0 | 0 | 0 | 0 | 0 | 0 |
| 39 | 11.2 | 0 | 0 | 0 | 0 | 0 | 0 | 0 | 0 | 0 | 0 | 0 |
| 40 | 11.2 | 2 | 3 | 0 | 2 | 4 | 1 | 0 | 0 | 0 | 0 | 1 |
| 40* | 11.2 | 2 | 4 | 0 | 1 | 4 | 0 | 0 | 0 | 0 | 0 | 3 |
| 41 | 11.2 | 0 | 0 | 0 | 0 | 0 | 0 | 0 | 0 | 0 | 0 | 0 |
| 42 | 11.2 | 0 | 3 | 3 | 1 | 4 | 0 | 0 | 0 | 0 | 0 | 0 |
| 42* | 11.2 | 0 | 4 | 4 | 1 | 4 | 0 | 0 | 0 | 0 | 0 | 0 |
| 43 | 11.2 | 1 | 3 | 0 | 1 | 4 | 1 | 0 | 0 | 0 | 0 | 0 |
| 43* | 11.2 | 1 | 1 | 1 | 1 | 4 | 1 | 0 | 0 | 0 | 0 | 0 |
| 44 | 11.2 | 4 | 3 | 0 | 1 | 3 | 0 | 0 | 0 | 0 | 0 | 0 |
| 44* | 11.2 | 4 | 4 | 0 | 1 | 4 | 0 | 0 | 0 | 0 | 0 | 0 |
| 45 | 11.2 | 4 | 3 | 1 | 1 | 3 | 1 | 0 | 0 | 0 | 0 | 0 |
| 45* | 11.2 | 4 | 4 | 1 | 1 | 3 | 1 | 0 | 0 | 0 | 0 | 0 |
| 46 | 11.2 | 4 | 4 | 3 | 3 | 4 | 3 | 0 | 0 | 0 | 0 | 0 |
| 46* | 11.2 | 4 | 4 | 3 | 3 | 4 | 3 | 0 | 0 | 0 | 0 | 0 |
| 47 | 11.2 | 4 | 3 | 3 | 2 | 3 | 1 | 1 | 1 | 1 | 1 | 1 |
| 47* | 11.2 | 4 | 4 | 3 | 2 | 3 | 1 | 1 | 1 | 1 | 1 | 0 |
| 48 | 11.2 | 0 | 2 | 1 | 2 | 4 | 0 | 0 | 0 | 0 | 0 | 0 |
| 49 | 11.2 | 0 | 3 | 1 | 1 | 3 | 0 | 0 | 0 | 0 | 0 | 0 |
| 49* | 11.2 | 0 | 4 | 1 | 2 | 3 | 1 | 0 | 0 | 0 | 0 | 0 |
| 50 | 11.2 | 2 | 3 | 0 | 1 | 4 | 0 | 0 | 0 | 0 | 0 | 0 |
| 50* | 11.2 | 2 | 3 | 0 | 1 | 4 | 0 | 0 | 0 | 0 | 0 | 0 |
| 51 | 11.2 | 2 | 2 | 0 | 1 | 2 | 1 | 0 | 0 | 0 | 0 | 0 |
| 51* | 11.2 | 1 | 3 | 0 | 1 | 3 | 0 | 0 | 0 | 0 | 0 | 0 |
| 52 | 11.2 | 4 | 3 | 2 | 2 | 3 | 1 | 2 | 0 | 1 | 0 | 0 |
| 52* | 11.2 | 4 | 4 | 2 | 2 | 3 | 1 | 3 | 0 | 0 | 0 | 0 |
| 53 | 11.2 | 4 | 3 | 2 | 1 | 3 | 1 | 0 | 0 | 0 | 0 | 0 |
| 53* | 11.2 | 4 | 3 | 1 | 1 | 3 | 1 | 0 | 0 | 0 | 0 | 0 |
| 54 | 11.2 | 4 | 2 | 3 | 3 | 3 | 1 | 1 | 0 | 0 | 0 | 0 |
| 54* | 11.2 | 4 | 3 | 4 | 4 | 4 | 1 | 1 | 1 | 0 | 1 | 0 |
| 55 | 11.2 | — | 2 | 3 | 3 | 4 | — | 0 | 0 | 0 | 0 | 0 |
| 56 | 11.2 | — | 3 | 1 | 3 | 3 | 4 | 0 | 0 | 0 | 0 | 1 |
| 57 | 11.2 | — | 3 | 1 | 2 | 4 | 3 | 0 | 0 | 0 | 0 | 1 |
| 58 | 11.2 | 1 | 2 | 0 | 2 | 1 | 1 | 0 | 0 | 0 | 0 | 0 |
| 59 | 11.2 | 1 | 2 | 0 | 1 | 4 | 0 | 0 | 0 | 0 | 0 | 0 |
| 59* | 11.2 | 1 | 2 | 0 | 1 | 4 | 0 | 0 | 0 | 0 | 0 | 0 |
| 60 | 11.2 | 2 | 2 | 2 | 2 | 4 | 0 | 0 | 0 | 0 | 0 | 0 |
| 60* | 11.2 | 4 | 2 | 1 | 1 | 4 | 0 | 0 | 0 | 0 | 0 | 0 |
| 61 | 11.2 | 1 | 0 | 0 | 1 | 2 | 0 | 0 | 0 | 0 | 0 | 0 |
| 62 | 11.2 | 4 | 4 | 3 | 3 | 4 | — | 1 | 0 | 1 | 0 | 1 |
| 62* | 11.2 | 4 | 4 | 4 | 4 | 4 | — | 1 | 0 | 0 | 0 | 1 |
| 63 | 11.2 | 1 | 3 | 0 | 1 | 4 | 0 | 0 | 0 | 0 | 0 | 0 |
| 63* | 11.2 | 2 | 2 | 0 | 1 | 4 | 0 | 0 | 0 | 0 | 0 | 1 |
| 64 | 11.2 | 0 | 0 | 0 | 1 | 0 | 0 | 0 | 0 | 0 | 0 | 0 |
| 65 | 11.2 | 0 | 0 | 0 | 1 | 0 | 0 | 0 | 0 | 0 | 0 | 0 |
| 66 | 11.2 | 2 | 1 | 2 | 2 | 0 | — | 0 | 0 | 1 | 0 | 0 |
| 67 | 11.2 | 3 | 0 | 0 | 0 | 0 | — | 0 | 0 | 0 | 0 | 0 |
| 68 | 11.2 | 3 | 1 | 0 | 1 | 3 | — | 0 | 0 | 0 | 0 | 0 |
| 68* | 11.2 | 4 | 1 | 0 | 1 | 4 | — | 0 | 0 | 0 | 0 | 0 |
| 70 | 11.2 | N | 2 | 0 | 1 | 1 | 0 | 1 | 1 | 1 | 0 | 2 |
| 70* | 11.2 | N | 2 | 1 | 1 | 1 | 0 | 0 | 0 | 0 | 0 | 2 |
| 71 | 11.2 | 0 | 2 | 0 | 1 | 0 | 1 | 0 | 0 | 0 | 1 | 2 |
| 71* |  | 0 | 2 | 0 | 1 | 0 | 0 | 0 | 0 | 0 | 0 | 1 |
| 72 | 11.2 | 4 | 4 | 3 | 2 | 3 | 2 | 0 | 0 | 0 | 0 | 1 |
| 72* |  | 4 | 4 | 3 | 2 | 3 | 3 | 0 | 0 | 0 | 0 | 1 |
| 73 | 11.2 | 4 | 2 | 2 | 3 | 3 | 2 | 1 | 0 | 0 | 0 | 0 |
| 73* |  | 4 | 1 | 2 | 2 | 3 | 1 | 0 | 0 | 0 | 0 | 0 |
| 74 | 11.2 | 4 | 3 | 3 | 1 | 3 | 1 | 1 | 0 | 0 | 0 | 0 |
| 74* |  | 4 | 4 | 3 | 1 | 3 | 1 | 1 | 0 | 0 | 0 | 0 |
| 75 | 11.2 | 4 | 2 | 0 | 2 | 0 | 1 | 0 | 0 | 0 | 0 | 1 |
| 75* |  | 4 | 2 | 0 | 2 | 1 | 0 | 0 | 1 | 0 | 1 | 1 |
| 76 | 11.2 | 1 | 3 | 1 | 2 | 0 | 0 | 1 | 1 | 0 | 0 | 2 |
| 76* |  | 1 | 4 | 0 | 1 | 1 | 0 | 0 | 0 | 0 | 0 | 1 |
| 77 | 11.2 | 1 | 0 | 1 | 2 | 0 | 1 | 0 | 0 | 2 | 0 | 0 |
| 78 | 11.2 | 1 | 2 | 0 | 2 | N | 1 | 0 | 0 | 0 | 0 | 0 |
| 79 | 11.2 | 0 | 2 | 1 | 2 | 3 | 2 | 0 | 0 | 0 | 0 | 0 |
| 80 | 11.2 | 0 | 1 | 0 | 0 | 0 | 0 | 0 | 0 | 0 | 0 | 0 |
| 81 | 11.2 | 0 | 0 | 0 | 0 | 1 | 0 | 0 | 0 | 0 | 0 | 0 |
| 82 | 11.2 | 0 | 0 | 0 | 0 | 0 | 0 | 0 | 0 | 0 | 0 | 0 |
| 83 | 11.2 | 0 | 0 | 0 | 0 | 0 | 0 | 0 | 0 | 0 | 0 | 0 |
| 84 | 11.2 | 0 | 0 | 0 | 0 | 0 | 0 | 0 | 0 | 0 | 0 | 0 |
| 85 | 11.2 | 0 | 0 | 0 | 0 | 0 | 0 | 0 | 0 | 0 | 0 | 0 |
| 86 | 11.2 | 0 | 0 | 0 | 0 | 1 | 0 | 0 | 0 | 0 | 0 | 1 |
| 87 | 11.2 | 0 | 0 | 0 | 0 | 0 | 0 | 0 | 0 | 0 | 0 | 0 |
| 88 | 11.2 | 0 | 1 | 0 | 1 | 1 | 0 | 0 | 0 | 0 | 0 | 1 |
| 89 | 11.2 | N | 3 | 3 | 2 | 4 | 2 | 1 | 2 | 0 | 1 | 3 |
| 90 | 11.2 | N | 3 | 1 | 1 | 3 | 2 | 1 | 1 | 0 | 1 | 2 |
| 91 | 11.2 | — | 0 | 0 | 0 | 0 | 0 | 0 | 0 | 0 | 0 | 0 |
| 92 | 11.2 | — | 0 | 0 | 1 | 0 | 0 | 0 | 0 | 0 | 0 | 0 |
| 93 | 11.2 | 0 | 0 | 0 | 1 | 1 | 0 | 0 | 0 | 0 | 0 | 0 |
| 94 | 11.2 | N | 1 | 0 | 1 | 3 | 0 | 0 | 0 | 0 | 0 | 1 |
| 95 | 11.2 | 0 | 0 | 0 | 1 | 0 | 0 | 0 | 0 | 0 | 0 | 1 |
| 96 | 11.2 | 0 | 0 | 0 | 1 | 2 | 0 | 1 | 0 | 0 | 0 | 0 |
| 97 | 11.2 | 0 | 1 | 0 | 1 | 1 | 0 | 1 | 0 | 1 | 0 | 1 |
| 98 | 11.2 | 0 | 1 | 0 | 1 | 0 | 0 | 1 | 0 | 0 | 0 | 1 |
| 99 | 11.2 | 0 | 0 | 0 | 3 | 1 | 0 | 1 | 0 | 0 | 0 | 1 |
| 100 | 11.2 | 0 | 1 | 1 | 1 | 3 | 0 | 0 | 0 | 0 | 0 | 1 |
| 101 | 11.2 | 1 | 0 | 0 | 0 | 3 | 0 | 0 | 0 | 0 | 0 | 1 |
| 102 | 11.2 | 1 | 0 | 0 | 0 | 3 | 0 | 0 | 0 | 0 | 0 | 0 |
| 103 | 11.2 | 0 | 0 | 0 | 0 | 3 | 0 | 0 | 0 | 0 | 0 | 1 |

Compounds of this invention were further tested to determine their post-emergent herbicidal activity on weeds in the presence of crop plants at various application rates. The procedure was the same as that for the preceding Table 4, except that the rate was varied as shown in the following Table 6. The plant species identification is the same as that given in Table 3.

TABLE 6
POST-EMERGENT ACTIVITY FOR WEEDS IN CROP PLANTS

| Example No. | Kg/ha | L | M | N | O | P | B | Q | D | R | E | F | C | J | S | K | T |
|---|---|---|---|---|---|---|---|---|---|---|---|---|---|---|---|---|---|
| 3 | 5.6 | 0 | 0 | 2 | 1 | 2 | 0 | 1 | 0 | 0 | 2 | 1 | 0 | 0 | 1 | 3 | 2 |
| 3* | 5.6 | 0 | 1 | 3 | 1 | 3 | 0 | 0 | 0 | 0 | 3 | 1 | 0 | 0 | 2 | 3 | 2 |
| 3 | 1.12 | 0 | 0 | 2 | 0 | 1 | 0 | 0 | 0 | 0 | 1 | 1 | 0 | 0 | 0 | 2 | 2 |
| 3* | 1.12 | 0 | 0 | 3 | 1 | 2 | 0 | 0 | 0 | 0 | 2 | 0 | 0 | 1 | 1 | 2 | 2 |
| 3 | 0.28 | 0 | 0 | 0 | 0 | 0 | 0 | 0 | 0 | 0 | 0 | 0 | 0 | 0 | 0 | 0 | 1 |
| 5 | 5.6 | 0 | 0 | 3 | 0 | 3 | 2 | 3 | 0 | 3 | 3 | N | 2 | 2 | 2 | 2 | 2 |
|  | 1.12 | 0 | 0 | 0 | 0 | 0 | 0 | 0 | N | 0 | 2 | N | 0 | 0 | 0 | 0 | 0 |
| 24 | 5.6 | 2 | 1 | 0 | 0 | 0 | 2 | 1 | 1 | 1 | 2 | 1 | 1 | 0 | 0 | 0 | 1 |
|  | 1.12 | 0 | 0 | 0 | 0 | 0 | 0 | 0 | 0 | 0 | 0 | 0 | 0 | 0 | 0 | 0 | 0 |
|  | 0.28 | 0 | 0 | 0 | 0 | 0 | 0 | 0 | 0 | 0 | 0 | 0 | 0 | 0 | 0 | 0 | 0 |
| 40 | 5.6 | 1 | 3 | 0 | 0 | 1 | 1 | 2 | 3 | 4 | 4 | 3 | 0 | 0 | 0 | 0 | 0 |
|  | 1.12 | 0 | 0 | 0 | 0 | 0 | 0 | 1 | 0 | 0 | 2 | 0 | 0 | 0 | 0 | 0 | 0 |
|  | 0.28 | 0 | 0 | 0 | 0 | 0 | 0 | 0 | 0 | 0 | 0 | 0 | 0 | 0 | 0 | 0 | 0 |
| 42 | 5.6 | 2 | 4 | 0 | 0 | 0 | 4 | 4 | 3 | 4 | 4 | 4 | 4 | 0 | 0 | 0 | 0 |
|  | 1.12 | 0 | 0 | 0 | 0 | 0 | 3 | 3 | 0 | 1 | 3 | 3 | 2 | 0 | 0 | 0 | 0 |
|  | 0.28 | 0 | 0 | 0 | 0 | 0 | 1 | 1 | 0 | 0 | 0 | 0 | 0 | 0 | 0 | 0 | 0 |
| 43 | 5.6 | 1 | 4 | 0 | 0 | 0 | 4 | 4 | 3 | 3 | 3 | 2 | 1 | 0 | 0 | 0 | 0 |
|  | 1.12 | 1 | 3 | 0 | 0 | 0 | 1 | 0 | 1 | 1 | 0 | 0 | 0 | 0 | 0 | 0 | 0 |
|  | 0.28 | 0 | 0 | 0 | 0 | 0 | 0 | 0 | 0 | 0 | 0 | 0 | 0 | 0 | 0 | 0 | 0 |
| 44 | 5.6 | 1 | 3 | 0 | 0 | 0 | 3 | 1 | 2 | 1 | 3 | 1 | 0 | 0 | 0 | 0 | 0 |
|  | 1.12 | 0 | 0 | 0 | 0 | 0 | 0 | 0 | 0 | 0 | 0 | 0 | 0 | 0 | 0 | 0 | 0 |
|  | 0.28 | 0 | 0 | 0 | 0 | 0 | 0 | 0 | 0 | 0 | 0 | 0 | 0 | 0 | 0 | 0 | 0 |

TABLE 6-continued
POST-EMERGENT ACTIVITY FOR WEEDS IN CROP PLANTS

| Example No. | Kg/ha | L | M | N | O | P | B | Q | D | R | E | F | C | J | S | K | T |
|---|---|---|---|---|---|---|---|---|---|---|---|---|---|---|---|---|---|
| 45 | 5.6 | 1 | 4 | 1 | 0 | 0 | 3 | 3 | 2 | 4 | 3 | 0 | 0 | 0 | 0 | 0 | 0 |
|  | 1.12 | 1 | 3 | 0 | 0 | 0 | 0 | 2 | 0 | 1 | 3 | 0 | 0 | 0 | 0 | 0 | 0 |
|  | 0.28 | 0 | 3 | 0 | 0 | 0 | 0 | 0 | 0 | 0 | 0 | 0 | 0 | 0 | 0 | 0 | 0 |
|  | 0.058 | 0 | 3 | 0 | 0 | 0 | 0 | 0 | 0 | 0 | 0 | 0 | 0 | 0 | 0 | 0 | 0 |
| 46 | 5.6 | 1 | 4 | 0 | 0 | 0 | 4 | 4 | 2 | 3 | 3 | 2 | 3 | 0 | 0 | 0 | 0 |
|  | 1.12 | 0 | 3 | 0 | 0 | 0 | 2 | 1 | 1 | 1 | 0 | 0 | 0 | 0 | 0 | 0 | 0 |
|  | 0.28 | 0 | 3 | 0 | 0 | 0 | 0 | 0 | 0 | 0 | 0 | 0 | 0 | 0 | 0 | 0 | 0 |
|  | 0.058 | 0 | 0 | 0 | 0 | 0 | 0 | 0 | 0 | 0 | 0 | 0 | 0 | 0 | 0 | 0 | 0 |
| 47 | 5.6 | 2 | 3 | 2 | 1 | 0 | 2 | 4 | 3 | 3 | 3 | 1 | 1 | 0 | 0 | 2 | 1 |
|  | 1.12 | 0 | 2 | 0 | 0 | 0 | 0 | 2 | 1 | 0 | 0 | 0 | 0 | 0 | 0 | 0 | 0 |
|  | 0.28 | 0 | 0 | 0 | 0 | 0 | 0 | 0 | 0 | 0 | 0 | 0 | 0 | 0 | 0 | 0 | 0 |
|  | 0.058 | 0 | 0 | 0 | 0 | 0 | 0 | 0 | 0 | 0 | 0 | 0 | 0 | 0 | 0 | 0 | 0 |
| 49 | 5.6 | 2 | 4 | 0 | 1 | 0 | 4 | 4 | 1 | 4 | 3 | 1 | 2 | 0 | 0 | 0 | 0 |
|  | 1.12 | 1 | 4 | 0 | 0 | 0 | 3 | 3 | 0 | 3 | 2 | 1 | 1 | 0 | 0 | 0 | 0 |
|  | 0.28 | 0 | 3 | 0 | 0 | 0 | 0 | 0 | 0 | 0 | 0 | 0 | 0 | 0 | 0 | 0 | 0 |
| 50 | 5.6 | 2 | 4 | 0 | 0 | 0 | 3 | 1 | 1 | 4 | 3 | 1 | 1 | 0 | 0 | 0 | 0 |
|  | 1.12 | 2 | 3 | 0 | 0 | 0 | 0 | 0 | 0 | 0 | 0 | 0 | 0 | 0 | 0 | 0 | 0 |
|  | 0.28 | 0 | 3 | 0 | 0 | 0 | 0 | 0 | 0 | 1 | 2 | 0 | 0 | 0 | 0 | 0 | 0 |
| 51 | 5.6 | 0 | 4 | 0 | 0 | 0 | 4 | 4 | 3 | 4 | 3 | 0 | 0 | 0 | 0 | 0 | 0 |
|  | 1.12 | 0 | 3 | 0 | 0 | 0 | 1 | 2 | 0 | 4 | 3 | 0 | 0 | 0 | 0 | 0 | 0 |
|  | 0.28 | 0 | 3 | 0 | 0 | 0 | 0 | 0 | 0 | 3 | 2 | 0 | 0 | 0 | 0 | 0 | 0 |
| 52 | 5.6 | 1 | 3 | 0 | 0 | 1 | 4 | 3 | 3 | 4 | 3 | 2 | 2 | 1 | 1 | 2 | 2 |
| 52* | 5.6 | 0 | 4 | 0 | 0 | 0 | 4 | 4 | 3 | 4 | 4 | 1 | 2 | 1 | 1 | 1 | 0 |
| 52 | 1.12 | 1 | 3 | 0 | 0 | 0 | 4 | 3 | 0 | 4 | 3 | 0 | 0 | 0 | 0 | 1 | 0 |
| 52* | 1.12 | 0 | 4 | 0 | 0 | 0 | 4 | 3 | 0 | 4 | 3 | 0 | 1 | 0 | 0 | 0 | 0 |
| 52 | 0.28 | 0 | 4 | 0 | 0 | 0 | 1 | 0 | 0 | 3 | 2 | 0 | 0 | 0 | 0 | 0 | 0 |
| 53 | 5.6 | 2 | 3 | 1 | 1 | 0 | 4 | 0 | 2 | 4 | 4 | 2 | 2 | 0 | 0 | 0 | 0 |
|  | 1.12 | 1 | 3 | 0 | 0 | 0 | 3 | 1 | 0 | 4 | 3 | 0 | 0 | 0 | 0 | 0 | 0 |
|  | 1.12 | 0 | 4 | 0 | 0 | 0 | 1 | 0 | 0 | 1 | 3 | — | 1 | 0 | 0 | 0 | 0 |
|  | 0.28 | 1 | 4 | 0 | 0 | 0 | 3 | 3 | 1 | 3 | 3 | 0 | 0 | 1 | 0 | 1 | 1 |
|  | 0.28 | 1 | 4 | 0 | 0 | 0 | 0 | 0 | 0 | 1 | 3 | — | 0 | 0 | 0 | 0 | 0 |
|  | 0.058 | 0 | 3 | 0 | 0 | 0 | 0 | 0 | 0 | 0 | 3 | — | 0 | 0 | 0 | 0 | 0 |
| 54 | 5.6 | 3 | 4 | 0 | 1 | 2 | 4 | 4 | 3 | 4 | 4 | 2 | 3 | 0 | 0 | 0 | 1 |
|  | 1.12 | 2 | 4 | 0 | 0 | 0 | 3 | 1 | 2 | 3 | 3 | 1 | 2 | 0 | 0 | 0 | 0 |
|  | 0.28 | 1 | 4 | 0 | 0 | 0 | 0 | 0 | 1 | 3 | 2 | 1 | 1 | 0 | 0 | 0 | 0 |
|  | 0.058 | 1 | 2 | 0 | 0 | 0 | 0 | 0 | 0 | 1 | 1 | 0 | 0 | 0 | 0 | 0 | 0 |
| 55 | 5.6 | 0 | 4 | 0 | 0 | 0 | 1 | 4 | 1 | 4 | 4 | — | 1 | 0 | 0 | 0 | 0 |
|  | 1.12 | 0 | 2 | 0 | 0 | 0 | 1 | 3 | 1 | 1 | 3 | — | 0 | 0 | 0 | 0 | 0 |
|  | 0.28 | 0 | 0 | 0 | 0 | 0 | 0 | 0 | 0 | 0 | 0 | — | 0 | 0 | 0 | 0 | 0 |
| 56 | 5.6 | 2 | 4 | 0 | 0 | 1 | 4 | 3 | 3 | 3 | 4 | 4 | 1 | 0 | 0 | 1 | 0 |
|  | 1.12 | 1 | 0 | 0 | 0 | 0 | 0 | 0 | 0 | 0 | 0 | 0 | 0 | 0 | 0 | 0 | 0 |
|  | 0.28 | 0 | 0 | 0 | 0 | 0 | 0 | 0 | 0 | 0 | 0 | 0 | 0 | 0 | 0 | 0 | 0 |
|  | 0.058 | 0 | 0 | 0 | 0 | 0 | 0 | 0 | 0 | 0 | 0 | 0 | 0 | 0 | 0 | 0 | 0 |
| 57 | 5.6 | 2 | 4 | 1 | 0 | 2 | 3 | 3 | 3 | 4 | 4 | 4 | 2 | 1 | 1 | 1 | 1 |
|  | 1.12 | 0 | 0 | 0 | 0 | 0 | 0 | 0 | 0 | 0 | 0 | 0 | 0 | 0 | 0 | 0 | 0 |
|  | 0.28 | 0 | 0 | 0 | 0 | 0 | 0 | 0 | 0 | 0 | 0 | 0 | 0 | 0 | 0 | 0 | 0 |
|  | 0.058 | 0 | 0 | 0 | 0 | 0 | 0 | 0 | 0 | 0 | 0 | 0 | 0 | 0 | 0 | 0 | 0 |
| 62 | 5.6 | 3 | 4 | 0 | 0 | 1 | 3 | 3 | 3 | 4 | 4 | — | 3 | 0 | 0 | 0 | 2 |
|  | 1.12 | 3 | 3 | 1 | 0 | 1 | 3 | 3 | 3 | 3 | 4 | — | 3 | 0 | 0 | 0 | 0 |
|  | 0.28 | 1 | 0 | 0 | 0 | 0 | 0 | 0 | 0 | 0 | 0 | — | 0 | 0 | 0 | 0 | 0 |
|  | 0.058 | 0 | 0 | 0 | 0 | 0 | 0 | 0 | 0 | 0 | 0 | — | 0 | 0 | 0 | 0 | 0 |
|  | 0.0112 | 0 | 0 | 0 | 0 | 0 | 0 | 0 | 0 | 0 | 0 | — | 0 | 0 | 0 | 0 | 0 |
| 63 | 5.6 | 1 | 3 | 0 | 0 | 0 | 2 | 3 | 1 | 3 | 3 | 2 | 1 | 0 | 0 | 0 | 0 |
|  | 1.12 | 0 | 0 | 0 | 0 | 0 | 0 | 0 | 0 | 0 | 0 | 0 | 0 | 0 | 0 | 0 | 0 |
|  | 0.28 | 0 | 0 | 0 | 0 | 0 | 0 | 0 | 0 | 0 | 0 | 0 | 0 | 0 | 0 | 0 | 0 |
| 71 | 5.6 | 1 | 2 | 0 | 0 | 1 | 0 | 1 | 0 | 0 | 0 | 0 | 0 | 0 | 0 | 0 | 0 |
|  | 1.12 | 0 | 0 | 0 | 0 | 0 | 0 | 0 | 0 | 0 | 0 | 0 | 0 | 0 | 0 | 0 | 0 |
| 72 | 5.6 | 0 | 3 | 0 | 0 | 0 | 4 | 3 | 2 | 4 | 4 | N | 3 | 0 | 0 | 0 | 0 |
|  | 5.6* | 0 | 3 | 0 | 0 | 0 | 4 | 3 | 2 | 4 | 4 | N | 3 | 0 | 0 | 0 | 0 |
|  | 1.12 | 0 | 3 | 0 | 0 | 0 | 1 | 2 | 1 | 2 | 1 | N | 1 | 0 | 0 | 0 | 0 |
|  | 1.12 | 0 | 3 | 0 | 0 | 0 | 1 | 0 | 0 | 2 | 1 | N | 1 | 0 | 0 | 0 | 0 |
|  | 0.28 | 0 | 0 | 0 | 0 | 0 | 0 | 0 | 0 | 0 | N | 0 | 0 | 0 | 0 | 0 | 0 |
|  | 0.058 | 0 | 0 | 0 | 0 | 0 | 0 | 0 | 0 | 0 | N | 0 | 0 | 0 | 0 | 0 | 0 |
| 73 | 5.6 | 1 | 3 | 0 | 0 | 0 | 3 | 3 | 1 | 3 | 3 | — | 2 | 0 | 0 | 0 | 0 |
|  | 1.12 | 1 | 2 | 0 | 0 | 0 | 1 | 1 | 1 | 2 | 2 | — | 0 | 0 | 0 | 0 | 0 |
|  | 0.28 | 0 | 0 | 0 | 0 | 0 | 2 | 2 | 0 | 0 | 0 | — | 0 | 0 | 0 | 0 | 0 |
| 74 | 5.6 | 1 | 4 | 0 | 1 | 0 | 3 | 3 | 2 | 3 | 4 | N | 3 | 0 | 0 | 0 | 0 |
|  | 5.6 | 1 | 4 | 0 | 1 | 0 | 3 | 3 | 1 | 3 | 4 | N | 3 | 0 | 0 | 0 | 0 |
|  | 1.12 | 0 | 0 | 0 | 0 | 0 | 1 | 0 | 0 | 2 | 2 | N | 0 | 0 | 0 | 0 | 0 |
|  | 0.28 | 0 | 0 | 0 | 0 | 0 | 0 | 0 | 0 | 0 | N | 0 | 0 | 0 | 0 | 0 | 0 |
|  | 0.058 | 0 | 0 | 0 | 0 | 0 | 0 | 0 | 0 | 0 | N | 0 | 0 | 0 | 0 | 0 | 0 |
| 75 | 5.6 | 0 | 2 | 0 | 0 | 0 | 3 | 2 | 1 | 2 | 2 | 1 | 1 | 0 | 0 | 0 | 0 |
|  | 1.12 | 0 | 0 | 0 | 0 | 0 | 0 | 0 | 0 | 0 | 0 | 0 | 0 | 0 | 0 | 0 | 0 |
|  | 0.28 | 0 | 1 | 0 | 0 | 0 | 0 | 0 | 0 | 0 | 0 | 0 | 0 | 0 | 0 | 0 | 0 |
| 76 | 5.6 | 2 | 3 | 0 | 0 | 2 | 3 | 2 | 2 | 4 | 4 | 3 | 1 | 0 | 0 | 0 | 0 |
|  | 1.12 | 0 | 1 | 0 | 0 | 0 | 0 | 0 | 0 | 0 | 0 | 0 | 0 | 0 | 0 | 0 | 0 |
|  | 0.28 | 0 | 0 | 0 | 0 | 0 | 0 | 0 | 0 | 0 | 0 | 0 | 0 | 0 | 0 | 0 | 0 |
| 89 | 5.6 | 2 | 0 | 0 | 3 | 1 | 1 | 1 | 0 | 2 | 2 | 1 | 1 | 0 | 0 | 0 | 0 |
|  | 1.12 | 0 | 0 | 0 | 0 | 0 | 0 | 0 | 0 | 0 | 0 | 0 | 0 | 0 | 0 | 0 | 0 |
|  | 0.28 | 0 | 0 | 0 | 0 | 0 | 0 | 0 | 0 | 0 | 0 | 0 | 0 | 0 | 0 | 0 | 0 |

TABLE 6-continued

| | | POST-EMERGENT ACTIVITY FOR WEEDS IN CROP PLANTS | | | | | | | | | | | | | | | |
|---|---|---|---|---|---|---|---|---|---|---|---|---|---|---|---|---|---|
| Example No. | Kg/ha | L | M | N | O | P | B | Q | D | R | E | F | C | J | S | K | T |
| | 0.056 | 0 | 0 | 0 | 0 | 0 | 0 | 0 | 0 | 0 | 0 | 0 | 0 | 0 | 0 | 0 | 0 |
| 90 | 5.6 | 2 | 3 | 3 | 0 | 3 | 2 | 2 | 2 | 2 | 1 | 2 | 2 | 3 | 2 | 3 | 2 |
| | 1.12 | 1 | 2 | 0 | 0 | 2 | 0 | 0 | 0 | 0 | 0 | 0 | 0 | 0 | 0 | 2 | 0 |
| 99 | 5.6 | 2 | 2 | 0 | 2 | 2 | 1 | 1 | 2 | 1 | 1 | 0 | 2 | 0 | 1 | 1 | 2 |
| | 1.12 | 1 | 1 | 0 | 0 | 0 | 0 | 0 | 1 | 0 | 0 | 0 | 0 | 0 | 0 | 0 | 3 |

The above tables illustrate one aspect of the present invention, that is, the use of the compounds of the invention to kill or injure undesirable plants, e.g., weeds.

Many of the 5-hydrogen-3-pyridinecarboxylates of this invention have utility as intermediates to herbicidal pyridine-3,5-dicarboxylates. Conversion of 3-pyridinecarboxylates of this invention to pyridine-3,5-dicarboxylates can be carried out by the following general procedure.

Example 77

3-Ethyl 5-Methyl 2,6-bis(trifluoromethyl)-4-isopropoxy-3,5-pyridinecarboxylate

This material was prepared as an oil, $n_D^{25}$ 1.4308, in 60% overall yield by first reacting 0.052 mol of product of Example 10 with 0.118 mol of LDA and excess of carbon dioxide to form 3-ethyl 2,6-bis(trifluoromethyl)-4-isopropoxy-3,5-pyridinecarboxylate followed by alkylating this product with methyl iodide according to the following general procedure. To a $-78°$ C. solution of 2.5 eq of LDA in DME was added a solution of 1 eq of starting material, the monocarboxylate product (Example 10) in dry DME. The resulting dark colored solution was stirred for 30 minutes at $-78°$ C. To the above solution was added excess of dry ice. The reaction mixture was stirred at $-78°$ C. for 15 minutes and warmed to room temperature in 1 hour. The reaction mixture was poured into ice water and extracted with ether. The aqueous layer was made acidic with HCl. The oil precipitate was extracted with ether. The ether extract was dried (MgSO4) and concentrated in vacuo to give the intermediate product, pyridine-3,5-dicarboxylic acid monoester. A mixture of 0.02 mol of the above 3,5-pyridinedicarboxylate acid monoester, 0.08 mol of the appropriate alkyl halide (methyl iodide), 0.04 mol of K2CO3, (methyl iodide), 0.04 mol of K2CO3, and 200 ml of acetone was held at reflux for 20 hours. The reaction mixture was filtered and concentrated. The residue was dissolved in ether. The ether solution was washed with 20% K2CO3, dried and concentrated. The residue was purified by HPLC or kugelrohr distillation to give the desired product.

Anal. Calc'd. for $C_{15}H_{15}F_6N_1O_4$: C, 44.68; H, 3.75; N, 3.47; Found: C, 45.07; H, 3.70; N, 3.53

Additional examples of 3,5-pyridinedicarboxylates prepared according to the above general procedure are listed in Table 7.

TABLE 7

3,5-Pyridinedicarboxylates

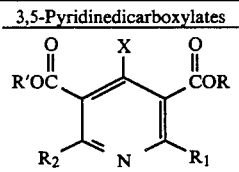

| Example | Starting Material | $R_1$ | $R_2$ | R | R' | X | $n_D^{25}$ | mp °C. |
|---|---|---|---|---|---|---|---|---|
| 78 | Product of Example 14 | $CF_3$ | $CF_2Cl$ | Et | Me | OiPr | 1.4484 | |
| 79 | Product of Example 11 | $CF_3$ | $CF_3$ | Et | Me | OEt | 1.4290 | |
| 80 | Product of Example 13 | $CF_3$ | $CF_2Cl$ | Et | Me | OEt | | 37.5–39.5 |
| 81 | Product of Example 21 | $CF_3$ | $CF_2Cl$ | Et | Me | Cl | | 57.5–59.5 |

The pre-emergent herbicidal activity of Examples 77–81 is listed in Table 8.

TABLE 8

| Pre-Emergence Herbicide Activity of Dicarboyxlates for Weeds | | | | | | | | | | | |
|---|---|---|---|---|---|---|---|---|---|---|---|
| Example No. | A | B | C | D | E | F | G | H | I | J | K |
| 77 | — | 2 | 3 | 3 | 3 | 3 | 3 | 3 | 3 | 3 | 3 |
| 78 | 3 | 2 | 3 | 3 | 3 | 3 | 2 | 3 | 3 | 3 | 3 |
| 79 | — | 1 | 3 | 3 | 3 | N | 2 | 3 | 3 | 3 | 3 |
| 80 | 3 | 1 | 3 | 3 | 3 | 3 | 1 | 3 | 3 | 3 | 3 |
| 81 | 0 | N | 0 | 0 | 0 | 0 | 0 | 3 | 0 | 1 | 3 |

As can be seen from the data above, some of the compounds appear to be quite safe on certain crops and can thus be used for selective control of weeds in these crops.

The herbicidal compositions of this invention, including concentrates which require dilution prior to application, may contain at least one active ingredient and an adjuvant in liquid or solid form. The compositions are prepared by admixing the active ingredient with an adjuvant including diluents, extenders, carriers, and conditioning agents to provide compositions in the form of finely-divided particulate solids, granules, pellets, solutions, dispersions or emulsions. Thus, it is believed that the active ingredient could be used with an adjuvant such as a finely-divided solid, a liquid of organic origin, water, a wetting agent, a dispersing agent, an emulsifying agent or any suitable combination of these.

Suitable wetting agents are believed to include alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, ditertiary acetylenic glycols, polyoxyethylene derivatives of alkylphenols (particularly isooctylphenol and nonylphenol) and polyoxyethylene derivatives of the mono-higher fatty acid esters of hexitol anhydrides (e.g., sorbitan). Preferred dispersants are methyl, cellulose, polyvinyl alcohol, sodium lignin sulfonates, polymeric alkyl naphthalene sulfonates, sodium naphthalene sulfonate, and polymethylene bisnaphthalene sulfonate.

Wettable powders are water-dispersible compositions containing one or more active ingredients, an inert solid extender and one or more wetting and dispersing agents. The inert solid extenders are usually of mineral origin such as the natural clays, diatomaceous earth and synthetic minerals derived from silica and the like. Examples of such extenders include kaolinites, attapulgite clay and synthetic magnesium silicate. The wettable powders compositions of this invention usually contain from above 0.5 to 60 parts (preferably from 5-20 parts) of active ingredient, from about 0.25 to 25 parts (preferably 1-15 parts) of wetting agent, from about 0.25 to 25 parts (preferably 1.0-15 parts) of dispersant and from 5 to about 95 parts (preferably 5-50 parts) of inert solid extender, all parts being by weight of the total composition. Where required, from about 0.1 to 2.0 parts of the solid inert extender can be replaced by a corrosion inhibitor or anti-foaming agent or both.

Other formulations include dust concentrates comprising from 0.1 to 60% by weight of the active ingredient on a suitable extender; these dusts may be diluted for application at concentrations within the range of from about 0.1-10% by weight.

Aqueous suspensions or emulsions may be prepared by stirring a nonaqueous solution of a water-insoluble active ingredient and an emulsification agent with water until uniform and then homogenizing to give stable emulsion of very finely-divided particles. The resulting concentrated aqueous suspension is characterized by its extremely small particle size, so that when diluted and sprayed, coverage is very uniform. Suitable concentrations of these formulations contain from about 0.1–60% preferably 5–50% by weight of active ingredient, the upper limit being determined by the solubility limit of active ingredient in the solvent.

Concentrates are usually solutions of active ingredient in water-immiscible or partially water-immiscible solvents together with a surface active agent. Suitable solvents for the active ingredient of this invention include dimethylformamide, dimethylsulfoxide, N-methyl-pyrrolidone, hydrocarbons, and water-immiscible ethers, esters, or ketones. However, other high strength liquid concentrates may be formulated by dissolving the active ingredient in a solvent then diluting, e.g., with kerosene, to spray concentration.

The concentrate compositions herein generally contain from about 0.1 to 95 parts (preferably 5-60 parts) active ingredient, about 0.25 to 50 parts (preferably 1-25 parts) surface active agent and where required about 4 to 94 parts solvent, all parts being by weight based on the total weight of emulsifiable oil.

Granules are physically stable particulate compositions comprising active ingredient adhering to or distributed through a basic matrix of an inert, finely-divided particulate extender. In order to aid leaching of the active ingredient from the particulate, a surface active agent such as those listed hereinbefore can be present in the composition. Natural clays, pyrophyllites, illite, and vermiculite are examples of operable classes of particulate mineral extenders. The preferred extenders are the porous, absorptive, preformed particles such as preformed and screened particulate attapulgite or heat expanded, particulate vermiculite and the finely-divided clays such as kaolin clays, hydrated attapulgite or bentonitic clays. These extenders are sprayed or blended with the active ingredient to form the herbicidal granules.

The granular compositions of this invention may contain from about 0.1 to about 30 parts by weight of active ingredient per 100 parts by weight of clay and 0 to about 5 parts by weight of surface active agent per 100 parts by weight of particulate clay.

The compositions of this invention can also contain other additaments, for example, fertilizers, other herbicides, other pesticides, safeners and the like used as adjuvants or in combination with any of the above-described adjuvants. Chemicals useful in combination with the active ingredients of this invention included, for example, triazines, ureas, carbamates, acetamides, acetanilides, uracils, acetic acid or phenol derivatives, thiolcarbamates, triazoles, benzoic acids, nitriles, biphenyl ethers and the like such as:

Heterocyclic Nitrogen/Sulfur Derivatives

2-Chloro-4-ethylamino-6-isopropylamino-s-triazine
2-Chloro-4,6-bis(isopropylamino)-s-triazine
2-Chloro-4,6-bis(ethylamino)-s-triazine
3-Isopropyl-1H-2,1,3-benzothiadiazin-4-(3H)-one 2,2 dioxide
3-Amino-1,2,4-triazole
6,7-Dihydrodipyrido(1,2-a:2',1'-c)-pyrazidiinium salt
5-Bromo-3-isopropyl-6-methyluracil 1,1'-Dimethyl-4,4'-bipyridinium
2-(4-isopropyl-4-methyl-5-oxo-2-imidazolin-2-yl)-3-quinolinecarboxylic acid
Isopropylamine salt of 2-(4-isopropyl-4-methyl-5-oxo-2-imidazolin-2-yl)nicotinic acid
Methyl 6-(4-isopropyl-4-methyl-5-oxo-2-imidazolin-2-yl)-m-toluate and methyl 2-(4-isopropyl-4-methyl-5-oxo-2-imidazolin-2-yl)-p-toluate

Ureas

N-(4-chlorophenoxy)phenyl-N,N-dimethylurea
N,N-dimethyl-N'-(3-chloro-4-methylphenyl)urea
3-(3,4-dichlorophenyl)-1,1-dimethylurea
1,3-Dimethyl-3-(2-benzothiazolyl)urea
3-(p-Chlorophenyl)-1,1-dimethylurea
1-Butyl-3-(3,4-dichlorophenyl)-1-methylurea
2-Chloro-N[(4-methoxy-6-methyl-3,5-triazin-2-yl)aminocarbonyl]-benzenesulfonamide
Methyl 2-(((((4,6-dimethyl-2-pyrimidinyl)amino)carbonyl)amino)sulfonyl)benzoate
Ethyl 2-[methyl 2-(((((4,6-dimethyl-2-pyrimidinyl)amino)carbonyl)amino)sulfonyl)]benzoate
Methyl-2((4,6-dimethoxy pyrimidin-2-yl)aminocarbonyl)amino sulfonyl methyl)benzoate
Methyl 2-(((((4-methoxy-6-methyl-1,3,5-triazin-2-yl)amino)carbonyl)amino)sulfonyl)benzoate

Carbamates/Thiolcarbamates

2-Chloroallyl diethyldithiocarbamate
S-(4-chlorobenzyl)N,N-diethylthiolcarbamate
Isopropyl N-(3-chlorophenyl)carbamate
S-2,3-dichloroallyl N,N-diisopropylthiolcarbamate
S-N,N-dipropylthiolcarbamate
S-propyl N,N-dipropylthiolcarbamate
S-2,3,3-trichloroallyl N,N-diisopropylthiolcarbamate

Acetamides/Acetanilides/Anilines/Amides

2-Chloro-N,N-diallylacetamide
N,N-dimethyl-2,2-diphenylacetamide

N-(2,4-dimethyl-5-[[(trifluoromethyl)sulfonyl]amino]-phenyl]acetamide
N-Isopropyl-2-chloroacetanilide
2',6'-Diethyl-N-methoxymethyl-2-chloroacetanilide
2'-Methyl-6'-ethyl-N-(2-methoxyprop-2-yl)-2-chloroacetanilide
α,α,α-Trifluoro-2,6-dinitro-N,N-dipropyl-p-toluidine
N-(1,1-dimethylpropynyl)-3,5-dichlorobenzamide

Acids/Esters/Alcohols 2,2-Dichloropropionic acid
2-Methyl-4-chlorophenoxyacetic acid
2,4-Dichlorophenoxyacetic acid
Methyl-2-[4-(2,4-dichlorophenoxy)phenoxy]propionate
3-Amino-2,5-dichlorobenzoic acid
2-Methoxy-3,6-dichlorobenzoic acid
2,3,6-Trichlorophenylacetic acid
N-1-naphthylphthalamic acid
Sodium 5-[2-chloro-4-(trifluoromethyl)phenoxy]-2-nitrobenzoate
4,6-Dinitro-o-sec-butylphenol N-(phosphonomethyl) glycine and its salts.
Butyl 2-[4-[(5-(trifluoromethyl)-2-pyridinyl)oxy]-phenoxy]-propanoate

Ethers 2,4-Dichlorophenyl-4-nitrophenyl ether
2-Chloro-α,α,α-trifluoro-p-tolyl-3-ethoxy-4-nitrodiphenyl ether
5-(2-chloro-4-trifluoromethylphenoxy)-N-methylsulfonyl 2-nitrobenzamide
1'-(Carboethoxy) ethyl 5-[2-chloro-4-(trifluoromethyl)-phenoxy]-2-nitrobenzoate

Miscellaneous 2,6-Dichlorobenzonitrile
Monosodium acid methanearsonate
Disodium methanearsonate
2-(2-chlorophenyl)methyl-4,4-dimethyl-3-isoxazolidinone
7-oxabicyclo (2.2.1) heptane, 1-methyl-4-(1-methyl ethyl)-2-(2-methylphenylmethoxy)-, exo- Fertilizers useful in combination with the active ingredients include, for example ammonium nitrate, urea, potash and superphosphate. Other useful additaments include materials in which plant organisms take root and grow such as compost, manure, humus, sand and the like.

Herbicidal formulations of the types described above are exemplified in several illustrative embodiments below.

| | | Weight Percent |
|---|---|---|
| I. Emulsifiable Concentrates | | |
| A. | Compound of Example No. 3 | 11.0 |
| | Free acid of complex organic phosphate of aromatic or aliphatic hydrophobe base (e.g., GAFAC RE-610, registered trademark of GAF Corp.) | 5.59 |
| | Polyoxyethylene/polyoxypropylene block copolymer with butanol (e.g., Tergitol XH, registered trademark of Union Carbide Corp.) | 1.11 |
| | Phenol | 5.34 |
| | Monochlorobenzene | 76.96 |
| | | 100.00 |
| B. | Compound of Example No. 14 | 25.00 |
| | Free acid of complex organic phosphate of aromatic or aliphatic hydrophobe base (e.g., GAFAC RE-610) | 5.00 |
| | Polyoxyethylene/polyoxypropylene block copolymer with butanol (e.g., Tergitol XH) | 1.60 |
| | Phenol | 4.75 |
| | Monochlorobenzene | 63.65 |
| | | 100.00 |
| II. Flowables | | |
| A. | Compound of Example No. 24 | 25.00 |
| | Methyl cellulose | 0.3 |
| | Silica Aerogel | 1.5 |
| | Sodium lignosulfonate | 3.5 |
| | Sodium N—methyl-N—oleyl taurate | 2.0 |
| | Water | 67.7 |
| | | 100.00 |
| B. | Compound of Example No. 18 | 45.0 |
| | Methyl cellulose | .3 |
| | Silica aerogel | 1.5 |
| | Sodium lignosulfonate | 3.5 |
| | Sodium N—methyl-N—oleyl taurate | 2.0 |
| | Water | 47.7 |
| | | 100.00 |
| III. Wettable Powders | | |
| A. | Compound of Example No. 5 | 25.0 |
| | Sodium lignosulfonate | 3.0 |
| | Sodium N—methyl-N—oleyl-taurate | 1.0 |
| | Amorphous silica (synthetic) | 71.0 |
| | | 100.00 |
| B. | Compound of Example 21 | 80.00 |
| | Sodium dioctyl sulfosuccinate | 1.25 |
| | Calcium lignosulfonate | 2.75 |
| | Amorphous silica (synthetic) | 16.00 |
| | | 100.00 |
| C. | Compound of Example No. 6 | 10.0 |
| | Sodium lignosulfonate | 3.0 |
| | Sodium N—methyl-N—oleyl-taurate | 1.0 |
| | Kaolinite clay | 86.0 |
| | | 100.00 |
| IV. Dusts | | |
| A. | Compound of Example No. 13 | 2.0 |
| | Attapulgite | 98.0 |
| | | 100.00 |
| B. | Compound of Example No. 10 | 60.0 |
| | Montmorillonite | 40.0 |
| | | 100.00 |
| C. | Compound of Example No. 54 | 30.0 |
| | Ethylene glycol | 1.0 |
| | Bentonite | 69.0 |
| | | 100.00 |
| D. | Compound of Example No. 62 | 1.0 |
| | Diatomaceous earth | 99.0 |
| | | 100.00 |
| V. Granules | | |
| A. | Compound of Example No. 52 | 15.0 |
| | Granular attapulgite (20/40 mesh) | 85.0 |
| | | 100.00 |
| B. | Compound of Example No. 70 | 30.0 |
| | Diatomaceous earth (20/40) | 70.0 |
| | | 100.00 |
| C. | Compound of Example No. 58 | 1.0 |
| | Ethylene glycol | 5.0 |
| | Methylene blue | 0.1 |
| | Pyrophyllite | 93.9 |
| | | 100.00 |
| D. | Compound of Example No. 46 | 5.0 |
| | Pyrophyllite (20/40) | 95.0 |
| | | 100.00 |

When operating in accordance with the present invention, effective amounts of the compounds of this invention are applied to the soil containing the seeds, or vegetative propagules or may be incorporated into the soil media in any convenient fashion. The application of liquid and particulate solid compositions to the soil can be carried out by conventional methods, e.g., power dusters, boom and hand sprayers and spray dusters. The compositions can also be applied from airplanes as a dust or a spray because of their effectiveness at low dosages.

The exact amount of active ingredient to be employed is dependent upon various factors, including the plant species and stage of development thereof, the type and condition of soil, the amount of rainfall and the specific compounds employed. In selective preemergence application or to the soil, a dosage of from about 0.02 to about 11.2 kg/ha, preferably from about 0.1 to about 5.60 kg/ha, is usually employed. Lower or higher rates may be required in some instances. One skilled in the art can readily determine from this specification, including the above examples, the optimum rate to be applied in any particular case.

The term "soil" is employed in its broadest sense to be inclusive of all conventional "soils" as defined in Webster's New International Dictionary, Second Edition, Unabridged (1961). Thus, the term refers to any substance or media in which vegetation may take root and grow, and includes not only earth but also compost, manure, muck, humus, sand, and the like, adapted to support plant growth.

Although the invention is described with respect to specific modifications, the details thereof are not to be construed as limitations.

What is claimed is:
1. A compound represented by the formula

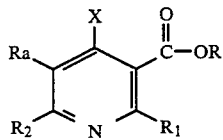

wherein:
R is selected from the group consisting of hydrogen, lower alkyl, lower alkenyl, lower alkynyl, haloalkyl, haloalkenyl, and a cation;
$R_1$ is trifluoromethyl;
$R_2$ is selected from fluorinated methyl, chlorofluorinated methyl, and fluorinated ethyl radicals;
Ra is selected from hydrogen and lower alkyl radicals; and X is —$OR_3$ in which $R_3$ is selected from hydrogen, lower alkyl, lower alkenyl, lower alkynyl, $C_3$-$C_6$ cycloalkyl, $C_3$-$C_6$ cycloalkylalkyl, haloalkyl, substituted or unsubstituted phenyl, substituted or unsubstituted phenylalkyl, dialkoxyphosphinyl, phenylsulfonyl, lower alkylcarbonyl, lower $C_3$-$C_6$ cycloalkylcarbonyl, pyrrolidinylcarbonyl, lower haloalkylcarbonyl, substituted or unsubstituted phenylcarbonyl, substituted or unsubstituted phenylalkylcarbonyl, substituted or unsubstituted phenoxyacetyl, substituted or substituted phenyl carbonyl methyl, carboalkoxymethyl, lower (dialkylamino)thioxo, lower dialkylaminocarbonyl, N-substituted or unsubstituted phenyl-N-alkylaminocarbonyl, lower alkoxyphosphinothioyl, and a cation, where in each foregoing occurrence of substituted phenyl the substituents are selected from the group consisting of halogens, nitro, lower alkyl, lower alkoxy, lower haloalkyl, lower haloalkoxy, and carbalkoxyalkoxy groups.

2. A compound according to claim 1 wherein $R_2$ is trifluoromethyl.
3. A compound according to claim 2 wherein Ra is H.
4. A compound according to claim 2 wherein Ra is lower alkyl.
5. A compound according to claim 1 wherein $R_2$ is chlorodifluoromethyl.
6. A compound according to claim 5 wherein Ra is H.
7. A compound according to claim 5 wherein Ra is lower alkyl.
8. A compound according to claim 1 wherein $R_2$ is difluoromethyl.
9. A compound according to claim 8 wherein Ra is H.
10. A compound according to claim 8 wherein Ra is lower alkyl.
11. A compound according to claim 1 wherein $R_3$ is carboalkoxymethyl.
12. A compound according to claim 1 wherein $R_1$ and $R_2$ are $CF_3$, Ra is hydrogen, R is methyl, and $R_3$ is selected from hydrogen and a cation.
13. 3-pyridinecarboxylic acid, 4-hydroxy-2,6-bis(trifluoromethyl)-, methyl ester, compound with N-(1-methylethyl)-2-propanamine.
14. 3-pyridinecarboxylic acid, 4-hydroxy-2,6-bis(trifluoromethyl)-, methyl ester, compound with 2-propanamine.
15. A herbicidal composition containing a carrier and an effective amount of a compound represented by the generic formula wherein:
R is selected from the group consisting of lower alkyl, lower alkenyl, lower alkynyl, haloalkyl, haloalkenyl, and a cation;
$R_1$ is trifluoromethyl;
$R_2$ is selected from fluorinated methyl, chlorofluorinated methyl, and fluorinated ethyl radicals;
Ra is selected from hydrogen and lower alkyl radicals; and
X is —$OR_3$ in which $R_3$ is selected from lower alkyl, lower alkenyl, lower alkynyl, $C_3$-$C_6$ cycloalkyl, $C_3$-$C_6$ cycloalkylalkyl, haloalkyl, substituted or unsubstituted phenyl, substituted or unsubstituted phenylalkyl, dialkoxyphosphinyl, phenylsulfonyl, lower alkylcarbonyl, lower $C_3$-$C_6$ cycloalkylcarbonyl, pyrrolidinylcarbonyl, lower haloalkylcarbonyl, substituted or unsubstituted phenylcarbonyl, substituted or unsubstituted phenylalkylcarbonyl, substituted or unsubstituted phenoxyacetyl, substituted or unsubstituted phenyl carbonylmethyl, carboalkoxymethyl, lower (dialkylamino)thioxo, lower dialkylaminocarbonyl, N-substituted or unsubstituted phenyl-N-alkylaminocarbonyl, lower alkoxyphosphinothioyl, and a cation, wherein in each foregoing occurrence of substituted phenyl the substituents are selected from the group consisting of halogens, nitro, lower alkyl, lower alkoxy, lower haloalkyl, lower haloalkoxy, and carbalkoxyalkoxy groups provided that when X is ethoxy, and $R_2$ is $CF_3$, Ra is not hydrogen, and when X is isopropoxy, Ra is not lower alkyl and R is not methyl, and further provided that X is not nitrophenoxy.

16. A composition according to claim 15 wherein $R_2$ is trifluoromethyl.

17. A composition according to claim 16 wherein Ra is H.

18. A composition according to claim 16 wherein Ra is lower alkyl.

19. A composition according to claim 15 wherein $R_2$ is chlorodifluoromethyl.

20. A composition according to claim 19 wherein Ra is H.

21. A composition according to claim 19 wherein Ra is lower alkyl.

22. A composition according to claim 15 wherein $R_2$ is difluoromethyl.

23. A composition according to claim 22 wherein Ra is H.

24. A composition according to claim 22 wherein Ra is lower alkyl.

25. A composition according to claim 15 wherein $R_3$ is carboalkoxymethyl.

26. A method of controlling the growth of undesirable vegetation comprising applying to the plant locus an effective amount of a compound represented by the generic formula

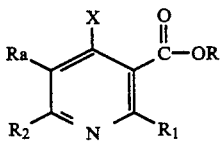

wherein:
R is selected from the group consisting of lower alkyl, lower alkenyl, lower alkynyl, haloalkyl, haloalkenyl, and a cation;
$R_1$ is trifluoromethyl;
$R_2$ is selected from fluorinated methyl, chlorofluorinated methyl, and fluorinated ethyl radicals;
Ra is selected from hydrogen and lower alkyl radicals; and
X is $-OR_3$ in which $R_3$ is selected from lower alkyl, lower alkenyl, lower alkynyl, $C_3$–$C_6$ cycloalkyl, $C_3$–$C_6$ cycloalkylalkyl, haloalkyl, substituted or unsubstituted phenyl, substituted or unsubstituted phenylalkyl, dialkoxyphosphinyl, phenylsulfonyl, lower alkylcarbonyl, lower $C_3$–$C_6$ cycloalkylcarbonyl, pyrrolidinylcarbonyl, lower haloalkylcarbonyl, substituted or unsubstituted phenylcarbonyl, substituted or unsubstituted phenylalkylcarbonyl, substituted or unsubstituted phenoxyacetyl, substituted or unsubstituted phenyl carbonylmethyl, carboalkoxymethyl, lower(dialkylamino)-thioxo, lower dialkylaminocarbonyl, N-substituted or unsubstituted phenyl-N-alkylaminocarbonyl, lower alkoxyphosphinothioyl, and a cation, where in each foregoing occurrence of substituted phenyl the substituents are selected from the group consisting of halogens, nitro, lower alkyl, lower alkoxy, lower haloalkyl, lower haloalkoxy, and carbalkoxyalkoxy groups, provided that when X is ethoxy and $R_2$ is $CF_3$, Ra is not hydrogen, and when X is isopropoxy, Ra is not lower alkyl and R is not methyl, and further provided that X is not nitrophenoxy.

27. A method according to claim 26 wherein $R_2$ is trifluoromethyl.

28. A method according to claim 27 wherein Ra is H.

29. A method according to claim 27 wherein Ra is lower alkyl.

30. A method according to claim 26 wherein $R_2$ is chlorodifluoromethyl.

31. A method according to claim 30 wherein Ra is H.

32. A method according to claim 30 wherein Ra is lower alkyl.

33. A method according to claim 26 wherein $R_2$ is difluoromethyl.

34. A method according to claim 33 wherein Ra is H.

35. A method according to claim 33 wherein Ra is lower alkyl.

36. A method according to claim 26 wherein $R_3$ is carboalkoxymethyl.

* * * * *